United States Patent [19]
Tobin et al.

[11] Patent Number: 6,099,847
[45] Date of Patent: Aug. 8, 2000

[54] CHIMERIC GAG PSEUDOVIRIONS

[75] Inventors: Gregory J. Tobin, Frederick, Md.; Matthew A. Gonda, Newtown Square, Pa.

[73] Assignee: The United States of America as represented by the Department of Health and Human Services, Washington, D.C.

[21] Appl. No.: 08/857,385

[22] Filed: May 15, 1997

Related U.S. Application Data

[60] Provisional application No. 60/020,463, May 16, 1996.

[51] Int. Cl.[7] .................................................. A61K 39/21
[52] U.S. Cl. ................................. 424/208.1; 424/192.1; 424/199.1; 435/235.1; 435/238; 435/320.1; 435/348; 530/350; 530/826; 536/23.1; 536/23.4; 536/23.5; 536/23.51; 536/23.72
[58] Field of Search .................................... 435/235, 236, 435/239, 348, 320.1, 948, 436, 475, 235.1, 238; 424/184.1, 187.1, 188.1, 204.1, 208.1, 450, 192.1, 199.1; 530/350, 826; 935/1, 6, 22, 23, 32, 47; 536/23.1, 23.4, 23.72, 24.1, 23.5, 23.51

[56] References Cited

PUBLICATIONS

Gonda and Oberste, *Control of Virus Diseases*, (Kurstak, E. Ed.) pp. 3–31 (1992).

Gonda, M.A., "Molecular Biology and Virus–Host Interactions of Lentiviruses[a]," *Annals of the New York Academy of Sciences*, 724: 22–42 (1994).

Gallo, R.C., "Human Retroviruses: A Decade of Discovery and Link with Human Disease," *The Journal of Infectious Diseases*, 164:235–43, (1991).

Levy, J.A., "Pathogenesis of Human Immunodeficiency Virus Infection," *Microbiology Reviews*, 57 (1):183–289 (Mar. 1993).

Mann, J.M., "Global AIDS into the 1990s," *Journal of Acquired Immune Deficiency Syndromes*, 3 (4):438–442 (1990).

Piot, p., et al., "The Global Epidemiology of HIV Infection: Continuity, Heterogeneity, and Change," *Journal of Acquired Immune Deficiency Syndromes*, 3(4):403–412 (1990).

Gallo, R.C., "Human retroviruses in the second decade: A personal perspective," *Nature Medicine*, 1 (8):753–759 (1995).

Daar, E.S., et al., "Transient High Levels of Viremia in Patients with Primary Human Immunodeficiency Virus Type 1 Infection," *The New England Journal of Medicine*, 324 (14):961–964 (1991).

Graziosi, C., et al., "Kinetics of human immunodeficiency virus type 1 (HIV–1) DNA and RNA synthesis during primary HIV–1 infection," *Proc. Natl. Acad. Sci. USA*, 90:6405–6409 (1993).

Borrow, P., "Virus–Specific CD8[+] Cytotoxic T–Lymphocyte Activity Associated with Control of Viremia in Primary Human Immunodeficiency Virus Type 1 Infection," *Journal of Virology*, 68 (9):6103–6110 (1994).

Pantaleo, et al., "Major expansion of CD8[+] T cells with a predominant Vβ usage during the primary immune response to HIV," *Nature*, 370:463–467 (1994).

(List continued on next page.)

*Primary Examiner*—Jeffrey Stucker
*Attorney, Agent, or Firm*—Townsend and Townsend and Crew LLP

[57] ABSTRACT

The present invention provides, inter alia, recombinant chimeric nucleic acids encoding a Gag-fs-fusion partner fusion protein; a pseudovirion comprising a retroviral Gag protein and a fusion partner, wherein the fusion partner is present in a Gag-fs-fusion partner fusion protein; an immunogenic composition comprising a pseudovirion; a Gag-fs-fusion partner fusion protein; and a method of making the pseudovirions of the present invention.

43 Claims, 2 Drawing Sheets

PUBLICATIONS

Koup, R.A., "Temporal Association of Cellular Immune Responses with the Initial Control of Viremia in Primary Human Immunodeficiency Virus Type 1 Syndrome," *Journal of Virology,* 68 (7):4650–4655 (1994).

Cao, Y. et al., "Virologic and Immunologic Characterization of Long–Term Survivors of Human Immunodeficiency Virus Type 1 Infection," *The New England Journal of Medicine,* 332 (4):201–208 (1995).

Klein, M. R., et al., "Kinetics of Gag–specific Cytotoxin T Lymphocyte Responses during the Clinical Course of HIV–1 Infection: A Longitudinal Analysis of Rapid Progressors and Long–term Asymptomatics," *J. Exp. Med.,* 181:1365–1372 (1995).

McFarland, E., et al., "Cytotoxic T Lymphocyte Lines Specific for Human Immunodeficiency Virus Type 1 Gag and Reverse Transcriptase Derived from a Vertically Infected Child," *The Journal of Infectious Diseases,* 167:719–23 (1993).

Gheysen, D., et al., "Assembly and Release of HIV–1 Percursor Pr55$^{gag}$ Virus–like Particles from Recombinant Baculovirus–Infected Insect Cells," *Cell,* 59:103–112 (1989).

Karacostas, V., et al., "Human immunodeficiency virus–like particles produced by a vaccinia virus expression vector," *Proc. Natl. Acad. Sci. USA,* 86:8964–8967 (1989).

Delchambre M., et al., "The GAG precursor of simian immunodeficiency virus assembles into virus–like particles," *The EMBO Journal,* 8 (9):2653–2660 (1989).

Rasmussen, L., et al., "Characterization of Virus–like Particles Produced by a Recombinant Baculovirus Containing the gag Gene of the bovine Immunodeficiency–like Virus[1]," *Virology,* 178:435–451 (1990).

Karacostas, V., et al., "Overexpression of the HIV–1 Gag––Pol Polyprotein Results in Intracellular Activation of HIV–1 Protease and Inhibition of Assembly an Budding of Virus–like Particles," *Virology,* 193:661–671 (1993).

Morikawa, S., et al., "Analyses of the Requirements for the Synthesis of Virus–like Particles by Feline Immunodeficiency Virus gag Using Baculovirus Vectors," *Virology,* 183:288–297 (1991).

Wagner, R., et al., "Studies on processing, particle formation, and immunogenicity of the HIV–1 gag gene product a possible component of a HIV vaccine," *Arch. Virol.,* 127:117–137 (1992).

Daniel et al. "High–titer Immune Responses Elicited by Recombinant Vaccinia Virus Priming and Particle Boosting Are Ineffective in Preventing Virulent SIV Infection", Aids Research and Human Retroviruses, vol. 10, No. 7 (Jul. 1994) pp. 839–851. RC607.A26.A35.

Truong et al. "Assembly and Immunogenicity of Chimeric Gag–Env Proteins Derived from the Human Immunodeficiency Virus Type 1", Aids Research and Human Retroviruses, vol. 12, No. 4(Mar. 1, 1995), pp. 291–301. RC607.A26.A35.

```
                        SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:

Phe Leu Gly Lys
1

(2) INFORMATION FOR SEQ ID NO:2:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

Glu Ala Leu Gly Ile Arg
1               5
```

(2) INFORMATION FOR SEQ ID NO:3:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

GAATTCGCGG CCGCCAGTGA CAATGAGAGT GAAG                    34

(2) INFORMATION FOR SEQ ID NO:4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

AGATCTCTTA AGTCTTATAG CAAAGCCCTT TC                      32

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

ACTAGCGGAG GCTAGAAGGA GAGAG                              25

(2) INFORMATION FOR SEQ ID NO:6:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

GTTTAAACGT TAACTTAATT ACTTGCTACG CGTTAGAGCT TCCTTTAGTT GCCCCCC      57

(2) INFORMATION FOR SEQ ID NO:7:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

CCGGTTAATT AATGGAATTA GGCCAGTAGT ATCAACT                  37

(2) INFORMATION FOR SEQ ID NO:8:

(i) SEQUENCE CHARACTERISTICS:
        (A) LENGTH: 36 base pairs

-continued

```
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:8:

GCATGTTTAA ACTGCTGCTC CTAAGAACCC AAGGAA                                    36
```

CHIMERIC GAG PSEUDOVIRIONS

CROSS REFERENCE TO RELATED APPLICATIONS

This application is a continuation-in-part of U.S. Ser. No. 60/020,463, filed May 16, 1996 By Tobin et al., which is incorporated herein by reference in its entirety.

FIELD OF THE INVENTION

The invention relates, inter alia, to cloning, retroviral vectors, cell mediated immunity, cancer vaccines and viral vaccines.

BACKGROUND OF THE INVENTION

The human immunodeficiency virus (HIV), a member of the lentivirus genus of retroviruses, is the causative agent of acquired immunodeficiency syndrome (AIDS) (review in Gonda, M. A., Ann. N. Y. Acad. Sci., 724:22–42 (1994); Gonda, et al., Control of Virus Diseases (Kurstak, E. Ed.), pp. 3–31 (1992); Gallo, R. C., J. Infect Dis., 164:235–243 (1991); Levy, J. A., Microbiol. Rev., 57:183–289 (1993)). HIV primarily infects CD4+ lymphocytes and macrophages. The depletion of CD4+ lymphocytes produces immune dysfunction that cripples the immune system's ability to fight opportunistic infections and cancers. Although extensive virologic, immunologic, and molecular characterizations have provided considerable insight into the biology and epidemiology of HIV, there are presently no effective treatments to reverse the disease process or vaccines to prevent infection. It is now known that HIV infection has reached pandemic proportions (Mann, J. M., J. Acquired Immune Def. Syndromes, 3:438–442 (1990); Piot, et al., J. Acquired Immune Def. Syndromes, 3:403–412 (1990)). Thus, the development of safe and effective vaccines and therapeutics remains a high priority in AIDS research (Gallo, R. C., Nature Medicine, 1:753–759 (1995)).

HIV is a protein-encapsidated positive-sense RNA virus that buds from the infected cell membrane. Its genome contains the obligate gag, pol and env structural genes flanked by the long terminal repeats, as well as a number of nonstructural regulatory genes (Gonda, et al., Control of Virus Diseases (Kurstak, E. Ed.), pp. 3–31 (1992); Levy, J. A., Microbiol. Rev., 57:183–289 (1993)). The gag gene encodes the Gag precursor, Pr55. The pol gene encodes proteins with enzymatic function (protease, reverse transcriptase, and endonuclease/integrase), while the env gene encodes the envelope glycoprotein precursor (gp160).

The HIV virion can be divided into two basic morphologic components: the viral core and envelope. The viral core consists predominantly of gag- and pol- encoded proteins and the viral RNA. In immature virions, the core consists primarily of uncleaved Pr55. Upon maturation of the virus, the viral protease cleaves Pr55 and products of pol into functional domains important in virus entry and replication. Pr55 is processed into the matrix (p17$^{Gag}$), capsid (p24$^{Gag}$), nucleocapsid (p7$^{Gag}$) and p6$^{Gag}$ proteins. The viral envelope consists of a lipid bilayer derived from the cell surface membrane into which gp160 is specifically concentrated. gp160 is cleaved by cellular proteases into the surface glycoprotein, gp120, which interacts with the cellular receptor, and the transmembrane glycoprotein, gp41, which anchors gp120 to the plasma membrane (Gonda, et al., Control of Virus Diseases (Kurstak, E., Ed.), pp. 3–31 (1992)).

In the initial phase of infection, HIV replicates rapidly and large quantities of virus are shed from infected cells; this is accompanied by destruction of effector cells (CD4+ lymphocytes) important in developing a competent immune response (Daar, N., Engl. J. Med., 324:961–964 (1991); Graziosi, et al., Proc. Natl. Acad. Sci. USA, 90:6405–6409 (1993); Borrow, et al., J. Virol., 68:6103–6110 (1994); Pantaleo, et al., Nature (London), 370:463–467 (1994)). The initial viremia passes into a subacute phase in which the activated immune system has apparently exerted some control over virus spread (Pantaleo, supra; Koup, et al., J. Virol., 68:4650–4655 (1994)). In the majority of HIV cases, the subacute phase of infection progresses to severe disease, which includes a depletion of CD4+ lymphocytes and the subsequent onset of opportunistic infections and AIDS. A small proportion of HIV-infected individuals appears to have a reduced virus load suggesting effective immunological control of the virus (Cao, et al., N. Engl. J. Med., 332:201–208 (1995)). It is thought that neutralizing antibodies and, perhaps more importantly, cytotoxic T-lymphocytes (CTLs) specific for HIV Gag and Env antigens may be of key importance in inhibiting virus spread and delaying pathogenesis (Klein, et al., J. Exp. Med., 181:1365–1372 (1995); McFarland, etal., J. Infect. Dis., 167:719–723 (1993)). A better understanding of the immunologic mechanisms by which HIV nonprogressors survive may provide clues to the nature of an appropriate protective immune response.

It was previously thought that both viral envelope and core components were necessary to make viral particles. Recent molecular studies on virus gene expression by heterologous promoters have shown that the gag-encoded precursor of retroviruses contains the minimal particle forming unit of the virus, and particle formation is independent of pol and env gene products in both mammalian and insect cell expression systems (Gheysen, et al., Cell, 59:103–112 (1989); Karacostas, et al., Proc. Natl. Acad. Sci. USA, 86:8964–8967 (1989); Delchambre, et al., EMBO. J., 8:2653–2660 (1989); Rasmussen, et al., Virology, 178:435–451 (1990); Karacostas, et al., Virology, 193:661–671 (1993); Morikawa, et al., Virology, 183:288–297 (1991); Wagner, et al., Arch. Virol., 127:117–137 (1992)). For HIV, expression of Pr55 by recombinant baculoviruses or vaccinia viruses results in the formation of nonreplicating, noninfectious, virus-like particles, or Gag pseudovirions, that lack genomic length viral RNA. The production of Gag pseudovirions in mammalian and insect cell systems using recombinant virus vectors provides a novel technology for engineering recombinant protein-based particulate vaccines for HIV and other viruses (Gheysen, et al., Cell, 59:103–112 (1989); Karacostas, et al., Proc. Natl. Acad. Sci. USA, 86:8964–8967 (1989); Delchambre, et al., EMBO. J., 8:2653–2660 (1989); Rasmussen, et al., Virology, 178:435–451 (1990); Karacostas, et al., Virology, 193, 661–671 (1993); Morikawa, et al., Virology, 183:288–297 (1991); Wagner, et al., Arch. Virol., 127:117–137 (1992)).

Recently, efforts have focused on developing strategies to package additional viral peptides and polyproteins into HIV Gag pseudovirions using the baculovirus insect cell expression system. It is thought that the incorporation of additional viral peptides and polyproteins may be advantageous in vaccine preparations, since they may contain important antigenic epitopes that may play a role in inducing protection from infection or disease. To date, however, such efforts have not been fully successful.

SUMMARY OF THE INVENTION

The present invention provides chimeric nucleic acids comprising a retroviral gag sequence, a target nucleic acid sequence derived from a nucleic acid encoding a fusion partner, and a frame shift site. Suitable fusion partners can be derived from any protein of interest which has a biological activity or which elicits a cellular or humoral immune response. Preferred fusion partners for inclusion in the recombinant nucleic acid include, but are not limited to, those derived from Env, inununomodulators, such as interleukins (e.g., IL-1, IL-2, IL-3, IL-4, IL-5, IL-6, IL-7, IL-8, IL-9, IL-10, IL-11, IL-12, IL-13, etc.), TNF, GM/CSF, nonretroviral viral antigens (e.g., a hepatitis protein such as the Hepatitis C core antigen), cancer antigens (e.g., MART-1, gp 100, tyrosinase, bcl-1, bcl-2, c-myc, int-2, hst-1, ras, p53, prostate-specific membrane antigen, and papilloma virus protein L1), molecules involved in signal transduction (e.g., protein kinase C and G proteins).

In a preferred embodiment, the present invention provides a recombinant chimeric gag-env nucleic acid, the chimeric gag-env nucleic acid comprising a retroviral gag sequence and a retroviral env sequence. Preferably, the sequences are in different reading frames. The gag and env sequences are transcribed from a single start site of transcription. The nucleic acid also has a frame-shift site. Several such sites are known, with the most preferred being the frameshift site which occurs in the gag-pol region of retroviral genomes. Modified or synthetic frameshift sites can be used to increase the frequency of translational frameshifting. In one embodiment, an optimized synthetic frameshift site is used.

Preferred env sequences comprise multiple domains of the Env protein. Most preferably, the entire Env protein is encoded by the selected env sequence. In one preferred embodiment, the env sequence encodes approximately the carboxyl 65% of a retroviral Env protein.

In one class of preferred embodiments, the recombinant chimeric nucleic acids are incorporated into a cloning vector or an expression vector. In one preferred embodiment, the nucleic acid is engineered for expression in an insect cell, which is a preferred system for making pseudovirions. For example, the recombinant chimeric nucleic acid can be expressed in a baculoviral vector. Baculoviral vectors are competent to transduce insect cells with target nucleic acids, such as the recombinant chimeric nucleic acids of the present invention. Nucleic acids are conveniently cloned into baculoviral vectors under the control of the strong polyhedron promoter. Transcribed nucleic acids typically have appropriate ribosome initiation sites, polyadenylation sites (e.g., SV40) and other features for proper expression. Nucleic acids are optionally designed for expression in mammalian cells.

The env, gag, pol and other retroviral sequences of the invention can be derived from many retroviral sources. Such sources include, but are not limited to, human immunodeficiency virus (HIV) type 1 (HIV-1), HIV type-2 (HIV-2), simian immunodeficiency virus (SIV), human t-cell lymphotropic virus (HTLV), murine leukemia virus (MULV) and many others known to persons of skill. Preferred sequences are derived from HIV and, most preferably, HIV-1.

The invention also provides pseudovirions made using Gag frame shift proteins. The pseudovirions contain a Gag protein (present as an independent protein species) and a Gag-frameshift-fusion partner fusion protein. As noted above, the fusion partner is derived from any protein of interest including, but not limited to, an immunomodulator, such as interleukin (e.g., IL-1, IL-2, IL-3, IL-4, IL-5, IL-6, IL-7, IL-8, IL-9, IL-10, IL-11, IL-12, IL-13, etc.), TNF, GM/CSF, a nonretroviral viral antigen (e.g., a hepatitis protein such as the Hepatitis C core antigen), a cancer antigen (e.g., MART-1, gp 100, tyrosinase, bcl-1, bcl-2, c-myc, int-2, hst-1, ras, p53, prostate-specific membrane antigen, and papilloma virus protein L1) and a molecule involved in signal transduction (e.g., protein kinase C and G proteins).

In one embodiment, the preferred fusion partner is an Env subsequence. In this embodiment, the pseudovirions include Gag-frameshift-Env (i.e., Gag-fs-Env) sequences. Preferably, all, or a large majority, of the Env protein is encoded in the Gag-fs-Env fusion protein. In one embodiment, approximately the carboxyl 65% of the Env protein is included in the Gag-fs-Env fusion protein. This particular construct is referred to herein as the Gag-fs-SU construct. Typically, from 50 to 100%, more typically from 60 to 100%, preferably from 65% to 100%, and more preferably from 75% to 100% of the Env protein is included in the fusion protein.

In one embodiment, particular Env domains are deleted in the frameshift fusions. For example, by deleting highly immunodominant epitopes from Env, it is possible to focus the immune response to smaller, more highly conserved epitopes.

In preferred embodiments, the Gag-fs-fusion partner fusion protein is localized to the interior of the pseudovirion. In preferred embodiments, the Env protein present in the pseudovirion elicits a cellular immune response (e.g., a cytotoxic t lymphocyte (CTL) response), but does not elicit a humoral immune response (e.g., antibodies are not generated against Env, i.e., antibodies generated against Env are not readily detectable using routine techniques) when administered to a mammal such as a mouse. This is particularly advantageous, because antibodies to Env can exacerbate retroviral infection by enhancing the interaction between the Env protein and the Env cellular target (e.g., the CD4+ receptor is the cellular target for Env).

It should be noted that although, in this particular embodiment, it is advantageous that the pseudovirion does not elicit a humor immune response, in other embodiments, it may be advantageous for the pseudovirion to elicit a humor immune response. Thus, it some instances it may be desirable for the pseudovirion to elicit both a cellular immune response and a humoral immune response. In addition, rather than eliciting a cellular and/or humoral response, it may be advantageous to use the pseudovirion as a delivery vehicle. For instance, a pseudovirion containing a GAG-fs-IL-2 fusion protein can be used as a delivery vehicle.

Immunogenic compositions and particulate vaccines are also provided by the present invention. In one embodiment, the immunogenic compositions and particulate vaccines comprise Gag-Env pseudovirions. In this embodiment, such immunogenic compositions, like the pseudovirions containing Gag-fs-Env, preferably elicit a cellular immune response against Env, without a corresponding humoral immune response. Although adjuvants are not required for immunogenicity of pseudovirions, adjuvants are optionally added to pseudovirions to provide an immunogenic composition. Immunogenic compositions and particulate vaccines optionally include water, pH buffers, salts, and osmotic balancing agents.

Other features, objects and advantages of the invention and its preferred embodiments will become apparent from the detailed description which follows.

BRIEF DESCRIPTION OF THE DRAWING

FIG. 1A and FIG. 1B show the organization of HIV sequences in baculovirus expression vectors. FIG. (A) HIV Gag; (B) HIV Gag-fs-SU. Predicted translations of HIV proteins (SEQ ID NOS: 1 and 2) expressed by polyhedron promoter in the vectors are shown below each construct. Bolded amino acids in (B) indicate predicted translation of chimeric Gag-fs-SU protein. Arrows (↓) indicate fusion protein junctions. Abbreviations are defined in text.

FIG. 2, Panels A–C, shows CTL responses of splenocytes from mice inoculated multiple times with HIV Gag or Gag-SU VLPs. Female Balb/c mice Were inoculated with 20 μg HIV Gag or GagSU VLPs in either PBS (solid lines and filled symbols) or Freund's adjuvant (dashed lines and open symbols) at three-week intervals. Splenocyte cultures were prepared after either 4 (Panel A) or 6 (Panels B and C) injections, antigen-stimulated in vitro, and assayed in triplicate for lysis of PA815 cells expressing either HIV Env (A and B) or Gag (C) precursor proteins by release of lactose dehydrogenase. Target cell lysis at varying ratios of effector to target cells was expressed as the percent total lysis from detergent disrupted target cells. Each line was derived from the mean percent lysis values derived from CLT assays of an individual mouse. In Panel C, lysis values represented by the symbols ◇, ◆, and ▶ were derived from mice inoculated with Gag-SU VLPs and symbols ● and o from mice inoculated with Gag VLPS. Lines sharing the same symbol between Panels B and C (◆, ◇, ▶) were derived from aliquots of splenocytes cultured from the same mice.

FIG. 3, Panels A and B Shows CTL responses of splenocytes from mice inoculated once with HIV Gag or Gag-SU VLPS. Female Balb/c mice were inoculated once with 20 μg HIV Gag (▲), 2 μg Gag (△), 20 μg Gag-SU (●), 2 μg Gag-SU VLPs in PBS (o), or PBS alone (□). Splenocyte cultures were prepared three weeks after inoculation, antigen-stimulated in vitro, and assayed for lysis of PA815 cells expressing either HIV Env (A) or Gag (B) precursor proteins by release of lactose dehydrogenase. Target cell lysis at varying ratios of effector to target cells was expressed as the percent total lysis from detergent disrupted target cells.

DEFINITIONS

Unless defined otherwise, all technical and scientific terms used herein have the same meaning as commonly understood by one of ordinary skill in the art to which this invention belongs. Singleton, et al. (1994) *Dictionary of Microbiology and Molecular Biology,* second edition, John Wiley and Sons (New York) provides one of skill with a general dictionary of many of the terms used in this invention. Although any methods and materials similar or equivalent to those described herein can be used in the practice or testing of the present invention, the preferred methods and materials are described. For purposes of the present invention, the following terms are defined below.

A "vector" is a composition which can transduce, transform or infect a cell, thereby causing the cell to express nucleic acids and/or proteins other than those native to the cell, or in a manner not native to the cell. A vector includes a nucleic acid (ordinarily RNA or DNA) to be expressed and/or replicated by the cell. A vector optionally includes materials to aid in achieving entry of the nucleic acid into the cell, such as a viral particle, liposome, protein coating or the like.

An "HIV-1-MN clone" is a clone derived from the publicly available HIV-1-MN genomic clone (Hall, et al. (1992) *J. Virol.* 66(9):5553–5560) by standard recombinant techniques such as subcloning, site-directed mutagenesis and the like, or, alternatively, an artificial nucleic acid synthesized based upon the HIV-1-MN genomic sequence.

A "promoter" is an array of nucleic acid control sequences which direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. The baculoviral polyhedron promoter is a well characterized promoter which directs expression of baculoviral genes in insect cells. The promoter is commonly used to control expression of heterologous nucleic acids in expression vectors in insect cells.

A "constitutive" promoter is a promoter which is active under most environmental and developmental conditions. An "inducible" promoter is a promoter which is under environmental or developmental regulation.

The terms "isolated" or "biologically pure" refer to material which is substantially or essentially free from components which normally accompany it as found in its native state. The native state for a pseudovirion is typically a cell culture.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence optionally includes the complementary sequence thereof.

The term "subsequence" in the context of a particular nucleic acid sequence refers to a region of the nucleic acid equal to or smaller than the specified nucleic acid.

The term "subsequence" in the context of a particular amino acid sequence refers to a region of the amino acid equal to or smaller than the full-length amino acid sequence of the specified protein. Thus, the fusion partners used in the fusion proteins of the present invention can be subsequences of any protein which has a biological activity or which elicits a cellular or humoral immune response. Typically, the subsequence is from 50 to 90%, more typically from 60 to 100%, preferably from 65 to 100%, and more preferably from 75 to 100% of the full-length amino acid sequence of the specified protein.

A virus or vector "transduces" a cell when it transfers nucleic acid into the cell. A cell is "transformed" by a nucleic acid when a nucleic acid transduced into the cell becomes stably replicated by the cell, either by incorporation of the nucleic acid into the cellular genome, or by episomal replication. A virus or vector is "infective" when it transduces a cell, replicates, and (without the benefit of any complementary virus or vector) spreads progeny vectors or viruses of the same type as the original transducing virus or vector to other cells in an organism or cell culture, wherein the progeny vectors or viruses have the same ability to reproduce and spread throughout the organism or cell culture.

A "recombinant chimeric nucleic acid" is an artificially constructed nucleic acid encoding heterologous nucleic acid subsequences. The term "heterologous" when used with reference to a nucleic acid indicates that the nucleic acid comprises two or more subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous. Similarly, a sequence from a gag gene is heterologous with reference to an env sequence when the two sequences are placed in a relationship other than the naturally occurring relationship of the nucleic acids in the retroviral genome.

The term "identical" in the context of two nucleic acid or polypeptide sequences refers to the residues in the two sequences which are the same when aligned for maximum correspondence. When percentage of sequence identity is used in reference to proteins or peptides it is recognized that residue positions which are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11–17 (1988) e.g., as implemented in the program PC/GENE (Intelligenetics, Mountain View, Calif., USA).

A "comparison window", as used herein, refers to a segment of at least about 50 contiguous positions, usually about 50 to about 200, more usually about 100 to about 150 in which a sequence is compared to a reference sequence of the same number of contiguous positions after the two sequences are optimally aligned.

Methods of alignment of sequences for comparison are well known in the art. Optimal alignment of sequences for comparison may be conducted by the local homology algorithm of Smith and Waterman (1981) *Adv. Appl. Math.* 2:482; by the homology alignment algorithm of Needleman and Wunsch (1970) *J. Mol. Biol.* 48:443; by the search for similarity method of Pearson and Lipman (1988) *Proc. Natl. Acad. Sci. USA* 85:2444; by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., USA); the CLUSTAL program is well described by Higgins and Sharp (1988) *Gene,* 73:237–244 and Higgins and Sharp (1989) *CABIOS* 5:151–153; Corpet, et al. (1988) *Nucleic Acids Research* 16:10881–90; Huang, et al. (1992) *Computer Applications in the Biosciences* 8:155–65, and Pearson, et al. (1994) *Methods in Molecular Biology* 24:307–31. Alignment is also often performed by inspection and manual alignment.

"Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in any described sequence. Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). See also, Creighton (1984) Proteins W. H. Freeman and Company.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* part I chapter 2 "overview of principles of hybridization and the strategy of nucleic acid probe assays", Elsevier, New York. Generally, highly stringent hybridization and wash conditions are selected to be about 5° C. lower than the thermal melting point ($T_m$) for the specific sequence at a defined ionic strength and ph. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2× SSC wash at 65° C. for 15 minutes (see, Sambrook, supra, for a description of SSC buffer). Often the high stringency wash is preceded by a low stringency wash to remove background probe signal. An example low stringency wash is 2× SSC at 40° C. for 15 minutes. In general, a signal to noise ratio of 2× (or higher) than that observed for an unrelated probe in the particular hybridization assay indicates detection of a specific hybridization.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

A nucleic acid is "derived" from a second nucleic acid when it is a subsequence of the second nucleic acid, or when it is engineered to encode the same amino acid sequence (i.e., by performing silent substitutions), or when the nucleic acids is a conservatively modified variation of the second nucleic acid.

A retroviral gag nucleic acid sequence is a nucleic acid derived from a nucleic acid sequence encoding a retroviral gag gene.

A "frame shift site" or "translation reading frame switching sequence" is a DNA or RNA sequence encoding an mRNA subsequence which is the site of a ribosomal frame shift during mRNA translation.

A "nonretroviral viral antigen" is a protein or protein subsequence derived from a virus other than a retrovirus.

A "cancer antigen" is a protein which is associated with a particular cancer type.

A "cytotoxic T lymphocyte response" is a cell-mediated immune response. CTL responses are typically measured by monitoring lysis of target cells by lymphocytes.

The activity of antigen presenting cells such as dendritic cells can be measured in an MLR or "mixed lymphocyte response" assay. In an MLR assay, the proliferative effect of antigen presenting cells (such as dendritic cells and macrophage) exposed to the pseudovirions of the invention is tested.

An "immunogenic composition" is a composition, typically comprising a protein or immunogenic peptide which induces a cell mediated immune response. An "immunogenic peptide" or "antigenic peptide" is a peptide which will bind an MHC allele to form an epitope recognized by a T cell, and which is capable of inducing a CTL response. Proteins are processed in antigen presenting cells into antigenic peptides and expressed on MHC receptors on the surface of antigen presenting cells. Thus, antigenic peptides are capable of binding to an appropriate MHC molecule and inducing a cytotoxic T cell response, e.g., cell lysis or specific cytokine release against the target cell which binds the antigen. Immunogenic compositions optionally include adjuvants, buffers, and the like.

A "particulate vaccine" is a composition comprising a pseudovirion. A pseudovirion is a lipid envelope structure which is a nonreplicating, noninfectious, virus-like particle lacking genomic length viral RNA. The pseudovirions of the invention typically contain a Gag protein (present as an independent protein species) and a Gag-frameshift-fusion partner fusion protein. The fusion partner is derived from any protein of interest including, but not limited to, an immunomodulator, such as interleukin (e.g., IL-1, IL-2, IL-3, IL-4, IL-5, IL-6, IL-7, IL-8,IL-9, IL-10, IL-11, IL-12, IL-13, etc.), TNF, GM/CSF, a nonretroviral viral antigen (e.g., a hepatitis protein such as the Hepatitis C. core antigen), a cancer antigen (e.g., MART-1, gp 100, tyrosinase, bcl-1, bcl-2, c-myc, int-2, hst-1, ras, p53, prostate-specific membrane antigen, and papilloma virus protein L1) and a molecule involved in signal transduction (e.g., protein kinase C. and G proteins).

DETAILED DESCRIPTION OF THE INVENTION AND PREFERRED EMBODIMENTS

Figure 1A:
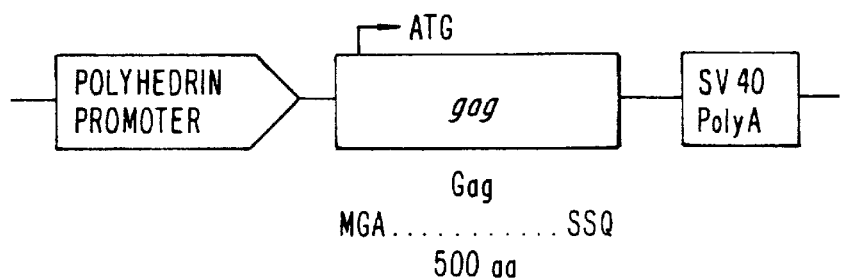
Figure 1B:
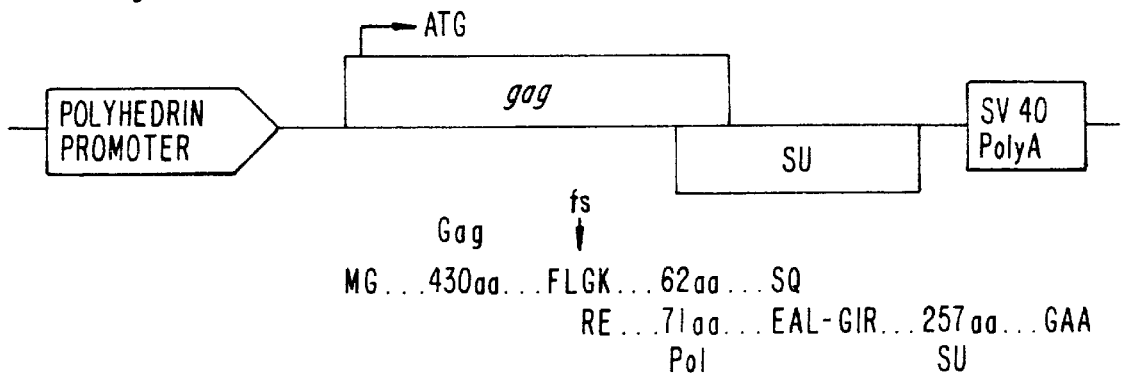

Gag pseudovirions are made using insect or other host cells. Because the pseudovirions do not package viral nucleic acids, the pseudovirions are noninfectious. Pseudovirions are used as antigenic compositions for the presentation of Gag antigens. The presentation of other retroviral antigens by the pseudovirions is desirable in many applications, such as vaccines and immunotherapeutics. Accordingly, the present invention provides Gag pseudovirions which comprise other retroviral components (e.g., Env proteins or subsequences of Env proteins) or other nonretroviral components as described herein. Similarly, cancer antigens are also expressed and presented using the pseudovirions of the invention.

A problem discovered in making Gag-Env pseudovirions was that Env proteins, when expressed separately from Gag proteins in cells used to make the pseudovirions, did not remain associated with the pseudovirions. Accordingly, strategies for co-expressing Env and Gag in pseudovirions were developed. In one embodiment, Gag and Env subsequences were co-expressed as a fusion protein, with the sequences in the same reading frame. This approach was generally unsatisfactory, as many of the Gag-Env subsequence fusion proteins failed to produce pseudovirions. Accordingly, a new strategy for expressing Gag-Env has now been developed. In one embodiment, Gag-Env fusion nucleic acids were produced, in which the Gag and Env domains of the nucleic acid were in different reading frames. A rare ribosomal reading frame shift during translation yields a percentage of fusion proteins with Gag and Env amino acid sequences. The majority of translated products do not produce Env sequences, but do provide Gag sequences. Formation of pseudovirions which comprise Gag and Env sequences was observed.

The strategy for making frame-shift Gag fusion proteins for pseudovirion formation is generally applicable to the expression of other retroviral and nonretroviral proteins in gag pseudovirions. Essentially, any fusion partner can be expressed in a gag pseudovirion by encoding the fusion protein in a nucleic acid and placing the nucleic acid encoding the fusion partner downstream from a frame shift site and a sequence which encodes Gag. For example, the fusion partner can be derived from an interleukin (IL-1, IL-2, IL-3, IL-4, IL-5, IL-6, IL-7, IL-8,IL-9, IL-10, IL-11, IL-12, IL-13, etc.), TNF, GM/CSF, a nonretroviral viral antigen (e.g., a hepatitis protein such as the Hepatitis C. core antigen), a cancer antigen (e.g., MART-1, gp 100, tyrosinase, bcl-1, bcl-2, c-myc, int-2, hst-1, ras, p53, prostate-specific membrane antigen, and papilloma virus protein L1), a molecule involved in signal transduction (e.g., protein kinase C. and G proteins). The frame shift site is preferably derived from the retroviral gag-pol frame shift site, but is optionally derived from other known frame-shifting sites, such as retrotransposon frame shifting sites, Ty element frame shifting sites, human astrovirus frame shifting sites, mouse intracisternal particles, etc.

In one embodiment, the frame shift site is a synthetic optimized frame shift site. For example, a set of similar retroviral gag-pol frame site sites are optionally made for a give fusion, for example, by synthesizing different gag-pol frame shift regions and cloning the sequences appropriately, or by site-directed mutagenesis of a given frameshift clone. The efficacy of the frame shift sites are assessed by measuring the production of any protein encoded downstream of the frameshift site (e.g., by ELISA or western blot analysis), typically normalized with respect to the production level of protein upstream of the frameshift site. The sequence which shows the highest frame shift activity (i.e., highest level of encoded downstream polypeptide relative to upstream polypeptide) is a synthetic "optimized" frameshift site for the set assessed. Alternatively, where a particular frameshift activity level is desired, a frameshift site from a particular set of possible frameshift sites which is closest to the desired activity level is considered to be "optimized."

Making Chimeric Nucleic Acids

In preferred embodiments, the chimeric nucleic acids of the present invention encode a Gag-frameshift-Env fusion protein. The Gag and Env sequences can be derived from any known retrovirus, including HIV, MuLV, SMRV, SFV, HFV, MMTV, SRVs, HTLV-I, HTLV-II, BLV, BIV, SIV, visna virus, EIAV, FIV, and EIAV. Most preferred sequences are derived from HIV, particularly HIV-1. Many retroviral clones, including HIV-1 clones, are well characterized and available. Well-established repositories of HIV (and other retroviral) sequence information include GenBank, EMBL, DDBJ and the NCBI. Well characterized HIV-1 clones include HXCB2, HIV-1-MN and HIV-1-MN-ST.1 (See, e.g., Hall, et al., *J. Virol.*, 66(9):5553–5560 (1992)).

Retroviral vector systems in general are known, including retroviral vectors based on such as HIV viruses, SIV viruses, murine retroviruses, gibbon ape leukemia viruses and combinations thereof. The frameshift nucleic acids of the invention optionally make use of the gag-pol frame shift region from any retrovirus (or other viral system). The most appropriate retroviral vector system are selected depending on the intended application. For instance, in raising an immune response against an antigen other than HIV, it may not be desirable to use an HIV pseudovirion, because patients immunized with the HIV-based pseudovirion would subsequently test sero ELSA analysis. Thus, prewestern blot or ELSA analysis. Thus, preferred vectors for stimulating CTL responses against cancer antigens include murine leukemia virus vectors, particularly murine leukemia virus vectors expressing gibbon ape leukemia virus envelopes, as well as vaccinia systems. Preferred vectors for treating HIV include HIV based vectors, as well as murine leukemia virus vectors expressing gibbon ape leukemia virus envelopes.

In this regard, murine retroviral vectors are well known in the art. The majority of the approved gene transfer trials in the United States rely on replication-defective retroviral vectors derived from murine retroviruses, such as murine moloney retrovirus (referred to alternately as MoLv MoMuLv or MuLv in the art) (see, e.g., Miller, et al. (1990) *Mol. Cell. Biol.* 10:4239; Kolberg R (1992) *J. NIH Res.* 4:43, and Cornetta et al. (1991) *Hum. Gene Ther.* 2:215). The major advantage of murine retroviral vectors for gene therapy are the high efficiency of gene transfer into certain types of replicating cells, the precise integration of the transferred genes into cellular DNA, and the lack of further spread of the sequences after gene transfer.

Murine vectors comprising Gibbon Ape Leukemia Virus envelopes are more broadly infective than Murine retroviruses such as Murine leukemia virus, and can be used to transduce many mammalian stem cells, including human stem cells. Gibbon Ape Leukemia Virus (GaLV) infects cells using the GaLV receptor, which is found on many cell types in many species (see, Johann, et al., *J. Virol.* 66:1635–1640 (1992)). GaLV can infect many mammalian species with the notable exception of mouse cells. The same receptor is used by simian sarcoma associated virus (SSAV), a strain of GaLV (see, Sommerfelt, et al., Virol. 176:58–59 (1990)).

The construction of hybrid virions having GaLV envelope proteins has been demonstrated. For instance, Wilson, et al., *J. Virol.* 63:2374–2378 (1989), describe preparation of infectious hybrid virions with GaLV and human T-cell leukemia virus retroviral env glycoproteins and the gag and pol proteins of the Moloney murine leukemia virus (MoMLV). In addition, Miller, et al., *J. Virol.* 65:2220–2224 (1991), describe construction of hybrid packaging cell lines that express GaLV envelope and MoMLV gag-pol proteins. Any of these vectors and methods of making retroviral clones can be applied to the present invention. In addition, retroviral elements are combined in packaging cell lines to provide necessary packaging components by transcomplementation. For example, GaLV retroviral packaging cell lines can be used to provide replication-defective hybrid virions for use in gene transfer in humans, hamsters, cows, cats, dogs, monkeys, chimpanzees, macaques, primates, and other species whose cells have host cell receptors for GaLV envelope proteins.

A number of standard techniques are used to ensure safety of retroviral vectors. For instance, a defective retroviral genome is introduced into the cell separately from the genes encoding the core and envelope components. In this way, recombination between the genome and the core and envelope genes, which would lead to the packaging of complete viral genomes, is extremely unlikely. The resulting virions therefore often do not comprise the gag, pol and env genes and are, thus, replication-defective. Homologous recombination, however, between the inserts can lead to the production of infectious virions. Typically, the packaging cells are produced by introducing the gag, pol and env genes on at least two separate plasmids. This scheme effectively prevents homologous recombination leading to reconstruction of infectious virus because the probability of multiple, independent homologous recombination events occurring is extremely low.

Retroviral vectors can also be designed to prevent synthesis of viral proteins by the integrated defective genome. For instance, if a portion of the gag gene is included to increase packaging efficiency, a stop codon can be introduced into the gene to prevent synthesis of gag proteins (see, Miller, et al., *BioTechniques* 7:982–988 (1989)).

In addition, the cells used to make packaging cells do not typically possess a cell receptor for the relevant vector and are, thus, not infectable by the vector. Thus, for instance, retroviral vector virions having the GaLV envelope cannot reinfect the packaging cells; thus, vector spread in the packaging cells is greatly reduced. Suitable packaging cells also have limited or no endogenous viral sequences. Cell lines for this purpose include, for example, the Mus dunni tail fibroblast cell line. This strategy decreases the potential for generation of recombinant vectors, which are often transmitted with higher efficiency than the parental vector.

HIV packaging systems are reported in Buchschacher, et al. (1992) *J. Virol.* 66(5):2731–2739; Rizvi, et al. (1993) *J. Virol.* 67(5):2681–2688; Carroll, et al. (1994) *J. Virol.* 68(9):6047–6051; Parolin, et al. (1994) *J. Virol.* 68(6):3888–3895; Shimada, et al. (1991) *J. Clin. Invest.* 88:10431047; and Richardson, et al. (1993) *J. Virol.* 67(7):3997–4005). HIV vectors are particularly useful for transducing $CD4^+$ cells. HIV cell transformation vectors can also be used to transduce non-dividing hematopoietic stem cells ($CD34^+$), e.g., by pseudotyping the vector. These stem cells differentiate into a variety of immune cells, including $CD4^+$ cells which are the primary targets for HIV infection. $CD34^+$ cells are a good target for ex vivo gene therapy, because the cells differentiate into many different cell types, and because the cells are capable of re-engraftment into a patient undergoing ex vivo therapy. The vesicular stomatitis virus envelope glycoprotein (VSV-G) has been used to construct VSV-G-pseudotyped HIV vectors which can infect hematopoietic stem cells (Naldini et al. (1996) *Science* 272:263 and Akkina et al. (1996) *J Virol* 70:2581).

Similarly, several groups have made pseudovirions using the particle formation proteins of nonretroviruses. Althought the majority of groups have used HIV Gag proteins to assemble noninfectious particles, others have used the Core Antigen of Hepatitis B Virus (Borisova et al. (1996) *Intervirology* 39:16–22), Papillomavirus L1 or L2 proteins (Sapp et al. (1996) *Intervirology* 39:62–71). However, none of these groups have packaged viral epitopes into the particles using frameshifting. Insertion of a frameshift element into these vectors results in a similar chimera to those described supra, except that the particle forming protein is different than the HIV Gag precursor. Thus, particle forming proteins of nonretroviruses are substituted for the Gag precursor.

In addition, as described, supra, stem cells are differentiated into antigen presenting dendritic cells expressing an antigen of choice, thereby eliciting a CTL response in vivo against a therapeutic target (e.g., a tumor antigen associated gene, or a viral antigen). Vectors comprising gibbon ape leukemia virus envelope proteins are also used for transformation of stem cells.

Retroviruses express their pol gene by a frameshifting mechanism (see, e.g., ten Dam, et al., CWRNA, 1(2):146–54 (1995); Renne, et al., *Virology,* 186(2):597–608 (1992); White and Fenner (1994) *Medical Virology, Fourth Edition (chapter* 35) Academic Press, San Diego; Rosenburg and Fauci (1993) in *Fundamental Immunology,* Third Edition Paul (ed) Raven Press, Ltd., New York (Rosenburg and Fauci 1); Jacks, et al., *Cell,* 55:447–458 (1988); Varmus, *Science,* 240:1427–1435 (1988); Battles, et al., *J. Virol,* 66:6868–6877 (1992); and the references therein. In cells infected with these viruses, the Gag and Gag-Pol precursor proteins are both translated from viral mRNA. Most translations terminate at the Gag stop codon. However, in roughly 5% of the translations, the ribosome undergoes a −1 frameshift that results in a shift from the Gag reading frame to the Pol reading frame.

In preferred embodiments, the Gag-Pol frame-shift region is used to make chimeric nucleic acids of the present invention. In preferred chimeric nucleic acids of the present invention, a nucleic acid encoding Gag and the frame shift region is recombinantly joined to a target nucleic acid which encodes a fusion partner (such as the Env protein or a subsequence thereof). Thus, the chimeric nucleic acid of the present invention has two products: (1) a Gag precursor and (2) a Gag fusion protein encoding Gag sequences and a fusion partner of interest (e.g., Env, an immunomodulatory protein, a cancer antigen or the like).

Although a full length Gag precursor sequence is preferred for use in the chimeric nucleic acids of the present invention, Gag is optionally deleted of subsequences without effecting the pseudoparticle forming ability of the resulting construct. For example, regions of the matrix protein (the N-terminal domain of the Gag polyprotein), regions of the capsid protein (p26) and regions of p6 (the C-terminal peptide of the Gag polyprotein) can be deleted while maintaining particle forming function, i.e., particle forming ability. See, Wang, et al., *J. Virol.,* 67(12):7067–76 (1993); Srinivasakumar, et al., *J. Virol.,* 69(10):6106–14 (1995); and Spearman, *J. Virol.,* 68(5):3232–42 (1994).

The fusion partner of interest is derived from any protein which has a biological activity or which elicits a cellular and/or immune response. In some embodiments, the fusion partner is a component of an infectious, immunomodulatory, cancerous or other process against which an elevated cellular response would be beneficial. The elevated cellular immune response is provided by incorporating the Gag-fs-fusion partner fusion proteins into pseudovirions of the invention and administering the resulting pseudovirions to a patient. Alternatively, the fusion partner can be an immunomodulator, e.g., IL-2, and, when incorporated into the pseudovirion, the pseudovirion is used as a delivery vehicle.

For instance, proteins which are differentially expressed in cancers, such as those associated with melanoma (e.g., MART-1, gp100, or tyrosinase; See, Zhai, et al., *J. Immunol.,* 156(2):700–10 (1996); Kawakami, et al., *J. Exp. Med.,* 180(1):347–52 (1994); and Topalian, et al., *Proc. Natl. Acad. Sci. USA,* 91(20):9461–5 (1994)) are beneficially expressed in the pseudovirions of the invention. Similarly, proteins associated with breast cancer (e.g., bcl-1, bcl-2, vasopressin related proteins; see, North, et al., *Breast Cancer Res. Treat.,* 34(3):229–35 (1995); Hellemans, Br. *J. Cancer,* 72(2):354–60 (1995); and Hurlimann, et al., *Virchows Arch.,* 426(2). 163–8 (1995)); and other carcinomas (e.g., c-myc, int-2, hst-1, ras and p53 mutants, prostate-specific membrane antigen (PSMA) and papiloma virus protein L1; see, Issing, et al., *Anticancer Res.,* 13(6B):2541–51 (1993); Tjoa, et al., *Prostate,* 28(1):65–9 (1996); Suzich, et al., *Proc. Natl. Acad. Sci. USA,* 92(25):11553–7 (1995); and Gjertsen, et al., *Lancet,* 346 (8987):1399–400 (1995)) are beneficially incorporated into the pseudovirions of the invention.

Immunomodulating agents such as cytokines and growth factors are expressed in an active form using the Gag-frame shift pseudovirions of the invention. Immunomodulating agents include IL-1, IL-2, IL-4, TNF, IL-6, interferons alpha, beta and gamma, and GM/CSF. See, Cao, et al., *Cancer Res. Clin. Oncol.,* 121(12):721–8 (1995); Dalgleish, *Gene Ther.,* 1(2):83–7 (1994); Suminami, et al., *J. Immunother Emphasis Tumor Immunol.,* 17(4):238–48 (1995); Abe, et al., *J. Cancer Res. Clin. Oncol.,* 121(9–10):587–92 (1995); Garbe and Krasagakis, *Invest. Dermatol.,* 100(2 Suppl):239S–244S (1993).

Viral epitopes other than retroviral Env can be expressed and packaged into the pseudoparticles of the invention. For example, viral structural proteins from infectious viruses are beneficially incorporated into the pseudovirions of the invention. For example, in a preferred embodiment, the Hepatitis C. virus core is encoded by the Gag-frame shift chimeric nucleic acids of the invention.

HIV Gag-Pol ribosomal frameshifting is estimated to occur between 1 and 5% of the time that the ribosome traverses the Gag-Pol frameshifting signals. Ribosomal frameshifting is used to express Pol or proteinase proteins in all other retroviruses, e.g., MuLV, SMRV, SFV, HFV, MMTV, SRVs, HTLV-I, HTLV-II, BLV, BIV, SIV, visna virus, EIAV, FIV, EIAV, etc. (see, ten Dam, et al. 1995, and Renne, et al. 1992, both supra). In addition, ribosomal frameshifting occurs in retrotransposons such as drosophila HeT-A, human astrovirus, mouse intracisternal particles, HERVs, and Ty elements of yeast. See, Danilevskaya, et al., *Chromosoma,* 103(3):215–24 (1994); Marczinke, et al., *J. Virol.,* 68(9):5588–95 (1994); Le, et al., *Genet. Anal. Tech. Appl.,* 8(7):191–205 (1991); and Mellor, et al., *Nature,* 318(6046):583–6 (1985). Such frameshift regions are optionally substituted for the preferred retroviral Gag-Pol frame shift site in the constructs of the invention.

The chimeric nucleic acids of the invention typically have a retroviral gag nucleic acid subsequence, a frame shift region and a second nucleic acid which encodes a protein such those described above. In certain embodiments, the nucleic acids also have a promoter, transcription termination sequences, polyadenylation sequences and the like to facilitate expression and processing of any encoded mRNA.

The chimeric nucleic acids of the present invention are optionally DNA, RNA, or mRNA. Most typically, the nucleic acids are provided by recombinantly making a DNA, which is expressed in a cell as RNA and/or as mRNA. Given the strategy for making the chimeric nucleic acids of the present invention, one of skill can construct a variety of clones containing functionally equivalent nucleic acids. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Berger and Kimmel, *Guide to Molecular Cloning Techniques, Methods in Enzymology,* volume 152, Academic Press, Inc., San Diego, Calif. (Berger); Sambrook, et al. (1989) *Molecular Cloning—A Laboratory Manual* (2nd ed.) Vol. 1–3, Cold Spring Harbor Laboratory, Cold Spring Harbor Press, N.Y., (Sambrook); and *Current Protocols in Molecular Biology,* F. M. Ausubel, et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

The nucleic acid compositions of this invention, whether RNA, cDNA, mRNA, genomic DNA, or a hybrid of the various combinations, are isolated from biological sources or synthesized in vitro. The chimeric nucleic acids of the present invention are present in transformed or transfected whole cells, in transformed or transfected cell lysates, or in a partially purified or substantially pure form.

In vitro amplification techniques suitable for amplifying sequences to provide a nucleic acid or for subsequent analysis, sequencing or subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis, et al., (1987) U.S. Pat. No. 4,683,202; PCR Protocols A Guide to Methods and Applications (Innis, et al. eds) Academic Press Inc. San Diego, Calif. (1990) (Innis); Arnheim & Levinson (Oct. 1, 1990) *C&EN* 36–47; *The Journal Of NIH Research* (1991) 3:81–94; (Kwoh, et al., *Proc. Natl. Acad. Sci. USA,* 86:1173 (1989); Guatelli, et al., *Proc. Natl. Acad. Sci. USA,* 87:1874 (1990); Lomell, et al., *J. Clin. Chem.,* 35:1826 (1989); Landegren, et al., *Science,* 241:1077–1080 (1988); Van Brunt, *Biotechnology,* 8:291–294 (1990); Wu and Wallace, Gene, 4:560 (1989); Barringer, et al., *Gene,* 89:117 (1990), and Sooknanan and Malek, *Biotechnology,* 13:563–564 (1995). Improved methods of cloning in vitro amplified nucleic acids are described in Wallace, et al., U.S. Pat. No. 5,426,039. Improved methods of amplifying large nucleic acids (up to 40 kb) are summarized in Cheng, et al., *Nature,* 369:684–685 (1994) and the references therein. One of skill will appreciate that essentially any RNA can be converted into a double stranded DNA suitable for restriction digestion, PCR expansion and sequencing using reverse transcriptase and a polymerase. See, Ausubel, Sambrook, Innis, and Berger, all supra.

Making Conservative Substitutions

One of skill will appreciate that many conservative variations of the nucleic acid constructs disclosed herein yield a functionally identical construct. For example, due to the degeneracy of the genetic code, "silent substitutions" (i.e., substitutions of a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence of a packaging or packageable construct are substituted with different amino acids with highly similar properties (see, the definitions section, supra) are also readily identified as being highly similar to a disclosed construct. Such conservatively substituted variations of each explicitly disclosed sequence are a feature of the present invention.

One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith, *Gene* 8:81–97 (1979), Roberts, et al., *Nature,* 328:731–734 (1987) and Sambrook, Innis, Ausubel, Berger, Needham VanDevanter and Mullis (all supra).

One of skill can select a desired gag-fs-env nucleic acid of the invention based upon the sequences provided and upon knowledge in the art regarding retroviruses. For example, the life-cycle, genomic organization, developmental regulation and associated molecular biology of HIV viruses have been the focus of over a decade of intense research. The specific effects of many mutations in the gag and env regions of the HIV genome are known. Moreover, general knowledge regarding the nature of proteins and nucleic acids allows one of skill to select appropriate sequences with activity similar or equivalent to the nucleic acids and polypeptides disclosed herein. Moreover, the definitions section herein describes exemplar conservative amino acid substitutions.

The nucleic acid sequence variants can be prepared with various objectives in mind, including facilitating purification and preparation of the recombinant polypeptides. The modified polypeptides are also useful for modifying plasma half-life, improving therapeutic efficacy, and lessening the severity or occurrence of side effects during therapeutic use. The sequence variants are usually predetermined variants not found in nature but which exhibit the same immunogenic activity as naturally occurring polypeptides. For instance, polypeptide fragments comprising only a portion (usually at least about 60–80%, typically 90–95%) of the naturally occurring structure are optionally produced. For use as vaccines, full-length polypeptides, or substantial fragments, incorporated into pseudovirions are typically preferred.

For example, the nucleic acid encoding the Gag-fs-SU protein described herein comprises the entire gag coding sequence, approximately the carboxyl 65% of the gp120 (SU) portion of the env protein (residues 255–524, corresponding to gp120 and the first ten residues of gp41), and the beginning of the Pol coding sequence (residues 1–79) in the region of the frame shift. The Gag portion is from HXB2 and the SU portion is from HIV$_{MN}$. Thus, the frameshift portion is from HXB2. Common conservative modifications of the nucleic acid encoding Gag-fs-SU include silent substitutions of the HXB2 or HIV$_{MN}$ sequences, substitution of the HXB2 or HIV$_{MN}$ sequences with those derived from a different HIV isolate, and minor modifications to the given sequences. Minor modifications include deletions in the nucleic acid encoding Gag which do not affect particle formation. In addition, minor modifications include conservative amino acid substitutions of the given sequences and the like.

Finally, most modifications to nucleic acids are evaluated by routine screening techniques in suitable assays for the desired characteristic. For instance, changes in the immunological character of encoded polypeptides can be detected by an appropriate immunological assay. For instance, changes in the cellular immunological character of the polypeptide can be detected by an appropriate CTL assay. Modifications of other properties such as nucleic acid hybridization to a complementary nucleic acid, redox or thermal stability of encoded proteins, hydrophobicity, susceptibility to proteolysis, or the tendency to aggregate are all assayed according to standard techniques.

In one example of a CTL assay, lymphocytes (effector cells) are removed from an immunized animal (or human) and tested for their ability to lyse target cells. frequently, the target cells are engineered to express one or more of the epitopes contained in the immunogen (e.g., a viral antigen, or a cancer antigen as described, supra.). The target and effector cells are from the same immunohistocompatibility group, i.e., they have the same MHC components on their surfaces. The lymphocytes from the immunized animal (effector cells) are incubated with the target cells. After approximately four hours, the mixed cultures are assayed for lysis of the target cells. Lysis is typically measured by th release of $^{51}Cr$ that had previously been taken up by the cells, or by the release of cytoplasmic proteins such as lactose dehydrogenase. Boehringer Mannheim (Indianapolis, Ind.) makes a kit (catalogue number 1644793) suitable for measuring lactose dehydrogenase release. An example of a target cell is a cell transduced with a viral vector encoding a target protein, e.g., a recombinant vaccinia virus vector encoding Gag or Env to test effector cell activity for effectors from animals immunized with a Gag-Env pseudovirion.

Making Pseudovirions

Sequences encoding the entire Gag precursor proteins of a variety of lentiviruses have been cloned behind the strong baculovirus polyhedron promotor in baculovirus transfer plasmids, incorporated into recombinant baculoviruses, and used to successfully make pseudovirions in insect cells. See, Madisen, et al., *Virology,* 158:248–250 (1987); Cheysen, et al., *Cell,* 69:103–112 (1989); Delchambre, et al., *EMBO. J.,* 8:2653–2660 (1989); Rasmussen, et al., *Virology,* 178:435–451 (1990); Morikawa, et al., *Virology,* 183:288–297 (1991); Wagner, et al., *Arch. Virol.,* 127:117–137 (1992); and Tobin, et al., *Methods in Molecular Genetics, Molecular Virology* (Adolph, K. W., ed.), Orlando, Academic Press, in press, vol. 4. As an example, FIG. 1 Panel A shows the gene structure and predicted translation of HIV gag in a baculovirus transfer plasmid. Essentially the same strategy is applied to make the pseudovirions of the invention, except that the chimeric nucleic acid of the invention, encoding a gag sequence, a frame shift sequence and a target sequence such as Env are used in place of a construct which only encodes Gag.

The transfer plasmids were co-transfected with AcMNPV DNA into Sf-9 insect cells and recombinant baculoviruses were isolated using standard methodologies. See, Tobin, et al., *Methods in Molecular Genetics, Molecular Virology* (Adolph, K. W., ed.), Orlando, Academic Press, in press, vol. 4; and Summers, et al., *Texas Agricultural Experiment Station Bulletin,* No. 1555, College Station, Tex., Texas Agricultural Experiment Station (1987). Expression of HIV Gag precursor proteins by the recombinant baculovirus results in their assembly into budding particles beneath the plasma membrane and the secretion of large quantities (1–10 mg/L culture supernatant) of virus-like particles. Because sequences encoding the retroviral protease were omitted from the HIV sequences expressed by the recombinant baculovirus, the pseudovirions are composed of unprocessed Gag precursor proteins and resemble immature HIV virions. See, Gonda, et al., *Science,* 227:173–177 (1985).

Gag pseudovirions can be purified readily from the culture supernatant by standard virologic techniques that include polyethylene glycol precipitation (PEG) and sucrose gradient sedimentation. See, Cheysen, et al., *Cell,* 69:103–112 (1989); Rasmussen, et al., *Virology,* 178:435–451 (1990); and Tobin, et al., *Methods in Molecular Genetics, Molecular Virology* (Adolph, K. W., ed.), Orlando, Academic Press, in press, vol. 4.

In the invention, pseudovirions are made by transducing a cell with the chimeric nucleic acid constructs of the invention. Most typically, the cell will be an insect or mammalian cell. The chimeric nucleic acids of the present invention are typically cloned into cloning and/or expression vectors for replication and/or expression of the Gag-fs-fusion partner fusion proteins of the present invention. The vectors of the invention are typically used to transduce insect or mammalian cells. However, because the vectors can be cloned into any cell type (e.g., to replicate the nucleic acid), the choice of the vector and expression control sequences to be included with a chimeric nucleic acid depends upon the intended application.

Examples of cells which can be transformed with the vectors of the invention include bacteria, yeast, plant, filamentous fungi, insect and vertebrate cells such as mammalian cells. It is expected that those of skill in the art are knowledgeable in the numerous expression systems available for cloning and expression of nucleic acids. Sambrook, Ausubel, and Berger provide a guide to expression cassettes, vectors and appropriate control sequences.

The culture of cells used in conjunction with the present invention, including cell lines and cultured cells from tissue or blood samples, including stem cells is well known in the art. Freshney (Culture of Animal Cells, a Manual of Basic Technique, third edition Wiley-Liss, New York (1994)) and the references cited therein provides a general guide to the culture of cells. See also, Kuchler, et al. (1977) *Biochemical Methods in Cell Culture and Virology,* Kuchler, R. J., Dowden, Hutchinson and Ross, Inc., and Inaba, et al., *J. Exp. Med.,* 176:1693–1702 (1992).

Insect cells are usually transformable by baculovirus. Suitable insect cell lines include mosquito larvae, silkworm, armyworm, moth and Drosophila cell lines such as a Schneider cell line (Schneider J. Embryol. Exp. Morphol. 27:353–365 (1987).

Mammalian cell systems often will be in the form of monolayers of cells although mammalian cell suspensions may also be used. Illustrative examples of mammalian cell lines include VERO and HeLa cells, Chinese hamster ovary (CHO) cell lines, WI38, BHK, COS cell lines or MDCK cell lines.

As indicated above, the vector, e.g., a plasmid, which is used to transform the host cell, preferably contains DNA sequences to initiate transcription and sequences to control the translation of the nucleic acid. These sequences are referred to as expression control sequences. When the host cell is of insect or mammalian origin illustrative expression control sequences are obtained from the SV-40 promoter (*Science*, 222:524–527, 1983), the CMV I.E. Promoter (*Proc. Natl. Acad. Sci.*, 81:659–663, 1984); baculovirus promoters, or the metallothionein promoter (*Nature*, 296:39–42, 1982). The cloning vector containing the expression control sequences is cleaved using restriction enzymes and adjusted in size as necessary or desirable and ligated with DNA coding for the gag fusion nucleic acids by means well known in the art.

Polyadenlyation or transcription terminator sequences from known mammalian genes are typically incorporated into the vector. An example of a terminator sequence is the polyadenlyation sequence from the bovine growth hormone gene, or the SV40 gene. Sequences for accurate splicing of the transcript are optionally included. An example of a splicing sequence is the VPI intron from SV40 (Sprague, J., et al., *J. Virol.*, 45: 773–781 (1983)).

Gene sequences to control replication in the cell may be incorporated into the vector, such as those found in bovine papilloma virus type-vectors. See, Saveria-Campo (1985), "Bovine Papilloma virus DNA a Eukaryotic Cloning Vector" in DNA Cloning Vol. II, a Practical Approach Ed. D. M. Glover, IRL Press, Arlington, Va. pp. 213–238.

The cells are competent or rendered competent for transformation by various means. There are several well-known methods of introducing DNA into animal cells. These include: calcium phosphate precipitation, fusion of the recipient cells with bacterial protorecipient caining the DNA, treatment of the recipient cells with liposomes containing the DNA, DEAB dextran, electroporation and microinjection of the DNA directly into the cells.

Uses for Pseudovirions and Fusion Proteins

As discussed, supra, the pseudovirions of the invention, which comprise fusion proteins of the invention, are typically used as vaccine or immunogenic compositions. The inoculation of Gag pseudovirions into mice, rabbits, and macaques results in strong humoral and cellular immune responses that do not require the use of adjuvants. See, Wagner, et al., *Arch. Virol.*, 127:117–137 (1992); and Tobin, et al., *Methods in Molecular Genetics, Molecular Virology* (Adolph, K. W., ed.), Orlando, Academic Press, in press, vol. 4.

The immune response of mice inoculated with Gag-fs-SU pseudovirions was evaluated. While the Gag component of pseudovirions induces strong humoral and CTL responses, the SU component of Gag-fs-SU pseudovirions elicits only a strong CTL response. Thus, the present results provide a role for chimeric Gag-fs-SU pseudovirions produced in the baculovirus insect cell system as vaccines and postinfection therapies.

In addition, the pseudovirions of the invention are optionally used in assays to detect antisera. For example, antisera to HIV in an individual indicates that the individual is infected with HIV. In standard HIV diagnostic tests, antisera to HIV are detected by monitoring binding of antisera to an HIV protein. The fusion proteins and pseudovirions of the invention are useful as sources of proteins for monitoring binding of antisera to the fusion proteins. Many methods of detecting antisera-protein interactions are known, including western blots, radiography, electrophoresis, capillary electrophoresis, high performance liquid chromatography (HPLC), thin layer chromatography (TLC), hyperdiffusion chromatography, and the like, immunological methods such as fluid or gel precipitin reactions, immunodiffusion (single or double), immunoelectrophoresis, radioirnmunoassays (RIAs), enzyme-linked immunosorbent assays (ELISAs), immunofluorescent assays, and the like. For a review of immunological and immunoassay procedures in general, see Stites and Terr (eds.) 1991 *Basic and Clinical Immunology* (7th ed.) and Paul, supra.

In some instances, the pseudovirions of the present invention optionally do not stimulate a humoral immune response against the protein downstream from Gag (e.g., Env). In other instances, it may desirable to have the pseudovirions of the present invention elicit a humoral immune response. In either instance, however, the fusion proteins of the invention are optionally expressed, purified (i.e., away from any surrounding pseudovirion envelope) and used to make antibodies. The antibodies are useful for detecting corresponding antigens in biological systems, such as cancer markers, viral epitopes, and the like. See, e.g., *Methods in Enzymology*, vol. 185, Academic Press, Inc., San Diego, Calif. (D. V. Goeddel, ed.) (1990) or M. Krieger, *Gene Transfer and Expression—A Laboratory Manual*, Stockton Press, New York, N.Y., (1990) and the references cited therein. For a discussion of how to make antibodies to selected antigens see, e.g., Coligan (1991) Current Protocols in Immunology Wiley/Greene, N.Y.; and Harlow and Lane (1989) *Antibodies: A Laboratory Manual*, Cold Spring Harbor Press, NY; Stites et al. (eds.) *Basic and Clinical Immunology* (4th ed.).

Dendritic cells are potent antigen presenting cells that activate quiescent T-lymphocytes against cells or viruses expressing the antigens presented by the dendritic cells. It was recently shown that dendritic cells transduced with a retroviral vector expressing a melanoma tumor associated antigen gene (MART-1) properly presented the MART-1 antigen, and that the resulting dendritic cells raised a strong CTL mediated anti-melanoma tumor response in vivo. See, Reeves, et al. (1996) *Cancer Research* 56:5672–5677. In a similar manner, the retroviral vectors of the present invention are used to raise, for example, an anti-tumor or an antiviral response (e.g., HIV or Herpes) in vivo by transducing dendritic cells with vectors encoding tumor or viral antigens (described, supra) in the frameshift region of the vector.

In brief, $CD43^+$ stem cells are isolated using standard techniques (e.g., by mobilization of $CD34^+$ cells into the peripheral blood by injection of granulocyte colony-stimulatory factor (GCF), e.g., by 1–5 daily injections of 10 μg GCF/kg patient mass), followed by lukapheresis. The stem cells are transduced with a retroviral virus like particles of the invention, e.g., by pseudotyping the vector with a VSV envelope protein (e.g., in a packaging cell line expressing a VSV envelope protein) and incubating the particles with the isolated cells. The transduced stem cells are differentiated in vitro into dendritic cells by incubating the cells with appropriate growth factors (e.g., GM-CSF, TNF-α, SCF). See, Reeves et al., id. MLR is optionally used to test the stimulatory function of the differentiated dendritic cells on allogenic quiescent T-cells (e.g., obtained by negative selection on an immunoaffinity column from peripheral blood cells obtained during leukapheresis, above). Dendritic cells from populations which are stimulatory to allogenic T-cells by MLR are introduced into a patient, e.g., by intravenous infusion.

MLR assays are a standard in vitro assay of antigen presenting function in cellular immunity. The assay measures the proliferation of T cells after stimulation by a selected cell type. The number of T cells produced are typically characterized by measuring T cell proliferation based on incorporation of 3H-thymidine in culture. Similar methods are used in vivo in nude or SCID mouse models. See also, Paul (supra) at chapter 31.

Assaying for Fusion Protein Components

A wide variety of formats and labels are available and appropriate for detection of fusion protein subsequences. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), western blot assays, immunofluorescent assays, and the like. Several commercially available ELISA assays for the detection of retroviral components, including Env domains, are available, allowing one of skill to detect Env in pseudovirion samples.

Similarly, the detection of the chimeric nucleic acids of the present invention proceeds by well known methods such as Southern analysis, northern analysis, gel electrophoresis, PCR, radiolabeling and scintillation counting, and affinity chromatography. Many assay formats are appropriate, including those reviewed in Tijssen (1993) *Laboratory Techniques in biochemistry and molecular biology—hybridization with nucleic acid probes* parts I and II, Elsevier, New York and Choo (ed) (1994) *Methods In Molecular Biology Volume 33—In Situ Hybridization Protocols,* Humana Press Inc., New Jersey (see also, other books in the Methods in Molecular Biology series); see especially, Chapter 21 of Choo (id.) "Detection of Virus Nucleic Acids by Radioactive and Nonisotopic in Situ Hybridization". Finally, PCR is also routinely used to detect nucleic acids in biological samples (see, Innis, supra, for a general description of PCR techniques).

In one preferred embodiment, antibodies are used to detect proteins incorporated into pseudovirions. Methods of producing polyclonal and monoclonal antibodies are known to those of skill in the art, and many anti-HIV antibodies are available. See, e.g., Coligan (1991) *Current Protocols in Immunology,* Wiley/Greene, NY; and Harlow and Lane (1989) *Antibodies: A Laboratory Manual,* Cold Spring Harbor Press, NY; Stites, et al. (eds.) *Basic and Clinical Immunology* (4th ed.), Lange Medical Publications, Los Altos, Calif., and references cited therein; Goding (1986) *Monoclonal Antibodies: Principles and Practice* (2d ed.), Academic Press, New York, N.Y.; and Kohler and Milstein, *Nature,* 256:495–497 (1975). Other suitable techniques for antibody preparation include selection of libraries of recombinant antibodies in phage or similar vectors. See, Huse, et al., *Science,* 246:1275–1281 (1989); and Ward, et al., *Nature,* 341:544–546 (1989). Specific monoclonal and polyclonal antibodies and antisera will usually bind with a $K_D$ of at least about 0.1 mM, more usually at least about 1 $\mu$M, preferably at least about 0.1 $\mu$M or better, and most typically and preferably, 0.01 $\mu$M or better.

Vaccines and Immunogenic Compositions

The vaccines and immunogenic compositions of the invention include the pseudovirions of the invention. Immunogenic compositions optionally further include components such as adjuvants to enhance immunogenicity, aqueous buffers, tracking dyes and the like. Vaccines minimally include the pseudovirions of the invention, and optionally include immunogenic components other than the pseudovirions of the invention, e.g., where a combinatorial vaccine is to be used. For example, the pseudovirions of the invention are optionally added to a standard vaccine against an infectious agent to enhance the efficacy of the standard vaccine.

Administering Pseudovirions and Vaccines

Pseudovirions containing therapeutic fusion proteins can be administered directly to the organism to elicit a cellular immune response in vivo. Administration is by any of the routes normally used for introducing a molecule into ultimate contact with blood or tissue cells. Pseudovirions containing Gag and Env protein subsequences are used to treat and prevent virally-mediated diseases such as AIDS in patients. Similarly, pseudovirions containing cancer protein subsequences are used to treat or prevent cancers.

Immunogenic compositions and vaccines which include the pseudovirions are administered in any suitable manner, preferably with pharmaceutically acceptable carriers. Suitable methods of administering such pseudovirions in the context of the present invention to a patient are available, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

The packaged nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and nonaqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. Parenteral administration and intravenous administration are the preferred methods of administration. The formulations of packaged nucleic acid can be presented in unit-dose or multi-dose sealed containers, such as ampules and vials. The packaged nucleic acids are not freeze-dried (lyophilized) because HIV particles are destroyed by lyophilization.

Injection solutions and suspensions can be prepared from sterile powders, granules, and tablets of the kind previously described. Cells transduced by the packaged nucleic acid as described above in the context of ex vivo therapy can also be administered intravenously or parenterally as described above.

The dose administered to a patient, in the context of the present invention should be sufficient to effect a beneficial therapeutic response in the patient over time, or to inhibit infection by a pathogen. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of diseases such as AIDS, the physician evaluates circulating virus levels, vector toxicities, progression of the disease, and the production of cellular immunity. In general, the dose equivalent of a naked fusion protein in pseudovirions is from about 1 $\mu$g to 10 mg for a typical 70 kilogram patient.

In the practice of this invention, compositions can be administered, for example, by intravenous infusion, orally, topically, intraperitoneally, intravesically or intrathecally. The preferred method of administration will often be intravenous, but the vectors can be applied in a suitable vehicle for the local and topical treatment of diseases. The pseudovirions of this invention can supplement treatment of any disease by any known conventional therapy, including cytotoxic agents, nucleotide analogues and biologic response modifiers.

For administration, pseudovirions can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

For treatment of disease, prior to infusion, blood samples are typically obtained and saved for analysis. Between 1 $\mu$g and 100 mg, more preferably 10 $\mu$g to 10 mg and, even more preferably about 1 mg of pseudovirions are infused intravenously over 60–200 minutes. Vital signs and oxygen saturation by pulse oximetry are closely monitored. Blood samples are obtained 5 minutes and 1 hour following infusion and saved for subsequent analysis. Leukopheresis, transduction and reinfusion are repeated every 2 to 3 months for a total of 4 to 6 treatments in a one year period. After the first treatment, infusions can be performed on a outpatient basis at the discretion of the clinician. If the reinfusion is given as an outpatient, the participant is monitored for at least 4, and preferably 8 hours following the therapy.

For prophylaxis, a single infusion is typically performed. Cellular immune responses are ordinarily monitored every 3 to 12 months to assess whether a booster dose of pseudovirions is needed.

If a patient undergoing infusion of a pseudovirion develops fevers, chills, or muscle aches, he/she receives the appropriate dose of aspirin, ibuprofen or acetaminophen. Patients who experience reactions to the infusion, such as fever, muscle aches, and chills are premedicated 30 minutes prior to the future infusions with either aspirin, acetaminophen, or diphenhydramine. Meperidine is used for more severe chills and muscle aches that do not quickly respond to antipyretics and antihistamines. Infusion is slowed or discontinued depending upon the severity of the reaction.

In addition to being directly administered, the pseudovirions of the invention are optionally used in ex vivo procedures. For example, antigen presenting cells are optionally isolated from a patient, exposed to the pseudovirions in vitro, and then re-infused into the patient. Typically, $10^7$ to $10^9$ cells are reinfused into the patient. The manner of re-infusion is ordinarily intravenous, and carried out over a period of 60–200 minutes.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Development of Non-infectious Particulate Vaccines for HIV

In this example, the initial studies on the development of recombinant methodologies for producing complex noninfectious particulate vaccines for HIV that contain Gag and Env epitopes, and the use of immunoelectron microscopy (IEM) in their structural characterization are described.

A. Materials and Methods

1. Virus and mammalian cell culture

Interleukin-2-independent CD4+ human lymphocyte cell (H9) (Popovic, et al., *Science*, 224:497–500 (1984) were maintained at densities between 0.5 and $3 \times 10^6$ cells/mi in RPMI 1640 medium supplemented with 7% fetal bovine serum and antibiotics in a humidified atmosphere of 5% CO at 37° C. Cells were aspirated daily to break up aggregates. HIV (strain-MN)-infected H9 cultures were obtained from the AIDS Vaccine Program (SAIC Frederick) and maintained as above. Several days prior to immunolabeling experiments, an equal number of uninfected H9 cells were added to the infected cell cultures to provide a mixed culture of acutely and chronically infected cells to enhance virus production.

2. Genetic engineering of recombinant baculoviruses

For these studies, the baculovirus *Autographica californica* multiply embedded nuclear polyhidrosis virus (AcMNPV) was used. Due to the large size of the AcMNPV genome (128 kb), foreign genes for expression were first cloned into a transfer plasmid that was then co-transfected with AcMNPV DNA into *Spodoptera frugiperda* (Sf-9) cells. Homologous recombination between transfer plasmid and AcMNPV DNA sequences introduces the foreign gene into the AcMNPV genome to create a recombinant baculovirus (Summers, et al., *A manual of methods for baculovirus vectors and insect cell culture procedures,* Texas Agricultural Experiment Station (1987); Tobin, et al., *Methods in*

*Molecular Genetics, Molecular Virology* (Adolph, K. W., Ed.), Academic Press (in press)). To generate HIV Gag and Env transfer plasmids (pVLHgag and pVLHenv, respectively), the sequences encoding either the entire HIV Gag or Env precursor protein were cloned behind the baculovirus polyhedron promoter in the PVL1392 and PVL1393 transfer plasmids (Invitrogen), respectively, using standard molecular biology protocols (Sambrook, et al., *Molecular Cloning: A Laboratory Manual,* second edition, Cold Spring Harbor Laboratory Press (1989)). For the construction of pVLHgag, the HIV gag sequences in pHIVhxb2 (Ratner, et al., *AIDS Res. Hum. Retroviruses,* 57–69 (1987)) were digested with NarI and HindI and treated with Klenow. The 1.8-kb gag fragment was gel isolated and ligated into the SmaI site of pVL1392. To make the env transfer vector, a 2.6-kb fragment coding the entire Env precursor glycoprotein was polymerase chain reaction amplified from a plasmid containing a complete proviral genome of HIV MN-ST1 (Lori, et al., *J. Virol.,* 66:5553–5560 (1992)), using the oligonucleotide forward primer GAATTCGCGGCCGCCAGTGACAAT-GAGAGTGAAG (nt 6222–6241) (SEQ ID NO: 3), which included unique EcoR1 and NotI sites (underlined) and the reverse primer AGATCTCTTAAGTCTTATAGCAAAGC-CCTTTC (nt 8810–8790) (SEQ ID NO: 4), which included unique BglII and AflII sites (underlined) to facilitate cloning. The oligonucleotide primers and coordinates were obtained from HIV sequences in the GenBank database (accession number M17449). The amplified product was cloned into pCRII (Invitrogen). The 2.6-kb env fragment was excised from pCRII using NotI and BaAI and subcloned directionally into the NotI and BglII and sites in pVL1393. DNA sequencing was used to confirm that no mutations were introduced during the polymerase chain reaction amplification or cloning steps.

Baculoviruses for the expression of Gag and Env precursors (AcMNPV-Hgag and AcMNPV-Henv, respectively) were derived individually by co-transfecting the transfer vectors pVLHgag or pVLHenv with wild-type AcMNPV DNA using the calcium phosphate precipitation method. Recombinant baculoviruses were isolated by limiting dilution and plaque purification techniques (Summers, et al., *A manual of methods for baculovirus vectors and insect cell culture procedures* (1987); Tobin, et al., *Methods in Molecular Genetics, Molecular Virology* (Adolph, K. W., Ed.), Academic Press (in press)).

3. Insect cell culture and baculovirus Infection

Uninfected Sf-9 cals were propagated as suspension cultures in Grace's medium (Life Technologies, Inc.) supplemented with 10% fetal bovine serum at room temperature. Cells were transferred to T-150 flasks (Costar) and infected or co-infected with recombinant baculoviruses at a multiplicity of infection of 5 plaque-forming units per cell. Cells were harvested 3 days postinfection for immunolabeling, as this was determined to be the peek day of pseudovirion or recombinant production.

4. Purification of Gag pseudovirions

Gag pseudovirions were purified from culture supernatants on the basis of their particulate nature and buoyant density (1.16 g/ml), using conventional virological methods (Rasmussen, et al., *Virology,* 178:435–451 (1990); Tobin, et al., *Methods in Molecular Genetics, Molecular Virology* (Adolph, K. W., Ed.), Academic Press (in press); Benton, et al., *In Vitro,* 14:192–199 (1978)). Three days postinfection, the supernatants were removed from cultures and clarified at 2,000×g for 15 min. Clarified supernatants were adjusted to 2.3% NaCl and 8% (w/v) polyethylene glycol 6000 (EM Science, Inc.), incubated overnight at 4° C., and centrifuged for 15 min at 5,000×g to collect the precipitate. The precipitates were resuspended in 10 mM Tris-HCI, pH 8.0, 1 mM EDTA, and 150 mM NaCl (TNE) and pelleted for 2 hr at 85,000×g through 10% sucrose (w/w) in TNE. Pelleted samples were resuspended in TNE and stored at 4° C. prior to immunoblot analysis. The above concentrating stops only partially purified pseudovirions; thus, they were still considered crude. In some cases, the crude preparations of chimeric HIV Gag+Env pseudovirions were further purified by sedimentation for 3 hr at 85,000×g in 10–60% (w/w) sucrose gradients prepared in TNE. The material sedimenting at 1.16 g/ml was collected, diluted in 3 volumes of TNE, repelleted, and resuspended in TNE.

5. Western blot analysis

The protein content of Gag pseudovirion and cell lysates was analyzed using standard immunoblotting techniques (Coligan, et al., *Current Protocols in Immunology,* Vol. 1, Wiley Interscience (1994); Tobin, et al., *J. Virol.,* 68:7620–7627 (1994)). For cell lysates, $2 \times 10^7$ cells were disrupted on ice in 2 ml TNE containing 0.1% NP-40 and 0.1% Triton X-100. The crude lysate was clarified by centrifugation at 18,000×g for 10 min and stored at −20° C. prior to analysis. Gag pseudovirions (0.1 μg) and cell lysates were denatured in Laemmli sample-loading buffer (Laemmli, U. K., *Nature* (London), 227:680–685 (1970)), electrophoresed in 10% polyacrylamide gels containing SDS, and electrophoretically transferred to PVDF (Millipore) membranes (Tobin, et al., *J. Virol.,* 68:7620–7627 (1994); Battles, et al., *J. Virol.,* 66:6868–6877 (1992)). The blots were incubated for 1 hr in a solution of 5% (w/w) non-fat dry milk in phosphate buffered saline (PBS), pH 7.2, containing 0.5 M NaCl and 0.1% Tween-20 (NT) and overnight in 1:2,000 dilutions of primary antibody with either a mouse monoclonal anti-HIV gp120 or anti-HIV p17$^{Gag}$ antibody in 0.5% non-fat dry milk in PBS-NT. Blots were washed 3 times in PBS-NT, 20 min each, and incubated for 1 hr in a 1:5,000 dilution of horseradish peroxidase-conjugated goat anti-mouse IgG antibody. The blots were then washed as above and incubated for 20 min in Enhanced ChemiLuminescent reagent (Amersham). HIV-specific protein were visualized by exposing the blots to XAR-5 film (Kodak) for periods of time 10 and 60 seconds.

6. Antibodies and colloidal gold conjugates

Indirect labeling was used for both cell-surface and postembedding IEM. Several polyclonal antisera and mouse monoclonal antibodies specific to HIV Gag or Env proteins were used as primary antibodies in this study (Table 1, infra). 15-nm colloidal gold-conjugated goat anti-rabbit IgG, goat anti-mouse IgG, goat anti-sheep IgG, and rabbit anti-goat IgG, and 10-nm colloidal gold-conjugated goat anti-mouse IgG (Amersham) were used as secondary antibodies. Normal antisera were used as controls for nonspecific binding of primary antibodies. Noninfected cells were also used as negative controls for immune sera. Prior to immunolabeling, all polyvalent primary antisera were incubated at 55° for 1 hr to inactivate serum complement activity.

TABLE 1

Primary anti-HIV antibodies and antisera used in indirect IEM

| Designation | Specificity | Species | Type |
|---|---|---|---|
| P8a9[a] | gp120$^{Env}$ | mouse | monoclonal |
| P3F5[a] | gp120$^{Env}$ | mouse | monoclonal |
| P5D3[a] | gp120$^{Env}$ | mouse | monoclonal |
| 3A3H3[a] | gp120$^{Env}$ | mouse | monoclonal |

TABLE 1-continued

Primary anti-HIV antibodies and antisera used in indirect IEM

| Designation | Specificity | Species | Type |
|---|---|---|---|
| G517[a] | gp120[Env] | goat | polyclonal |
| G363[b] | gp120[Env] | goat | polyclonal |
| S567[b] | gp120[Env] | sheep | polyclonal |
| D3D9[a] | p17[Gag] | mouse | monoclonal |
| P1F5[a] | p24[Gag] | mouse | monoclonal |
| anti-p24[a] | p24[Gag] | rabbit | polyclonal |
| anti-Pr55[c] | Pr55[Gag] | rabbit | polyclonal |

[a]Obtained from S. Nigida, AIDS Vaccine Program, SAIC Frederick, Frederick, MD.
[b]Obtained from NIH AIDS Research and Reference Reagent Program, Rockville, MD.
[c]Antisera raised against recombinant Pr55[Gag] produced in insect cells by AcMNPV-Hgag recombinant baculovirus.

7. IEM

Cell-surface labeling. Cell-surface labeling was performed on viable cells. The procedures for immunolabeling noninfected and HIV-infected H9 and noninfected and recombinant AcMNPV-infected Sf-9 cells were identical. To minimize distortion of cell morphology, internalization of antibody molecules, and release of virus particles from labeled cells, all wash buffers and antibody-containing solutions were pre-chilled and incubations and centrifugations were performed at 4° C. Recombinant AcMNPV-infected Sf-9 and HIV-infected H9 cells were handled under biological safety levels 2 and 3, respectively. All wash buffers consisted of PBS, pH 7.2 containing 0.1% (w/v) bovine serum albumin (BSA). Monoclonal (mouse) or polyclonal (goat, rabbit, and sheep) antibodies were diluted just prior to the beginning of the experiment in wash buffer. The colloidal gold-conjugated antibodies (goat anti-mouse IgG, goat-rabbit IgG, rabbit anti-sheep IgG, and rabbit anti-goat IgG) were diluted with Tris-buffered saline (TBS), 20 mM Tris (pH 8.2), and 150 mM sodium chloride, containing 0.1% BSA. Incubations with secondary antibodies were performed in Tris buffers as colloidal gold-conjugated antibodies often flocculate in solutions containing phosphates. For each labeling reaction, $2 \times 10^7$ cells (infected or noninfected) were gently pelleted (150×g for 5 min), and cell pellets were resuspended in wash buffer containing 10% normal serum from goat or rabbit, matching the species of the secondary antibody to reduce the nonspecific binding of antibodies in subsequent labeling reactions. After 1 hr of blocking, the cells were pelleted as above and the majority of the supernatant was gently removed without air drying the pellet. The pellet was resuspended and incubated for 1 hr in 200 µl of primary antibody with periodic gentle agitation. The calls were resuspended in 5 ml of wash buffer and pelleted. This procedure was repeated twice. The final pellet was resuspended in TBS with 0.1% BSA and incubated for 1 hr with periodic agitation in a 1:20 dilution of colloidal gold-conjugated secondary antibody containing a 1:20 dilution of species matched normal serum. 5 ml of TBS with 0.1% BSA was added and the cells were pelleted. The washing procedure was repeated once with wash buffer and then PBS alone to remove excess Tris and BSA prior to fixation with glutaraldehyde and preparation for electron microscopy.

For electron microscopy, 4 ml of a buffered fixative solution containing 1.25% glutaraldehyde, 0.1 M sodium cacodylate, and 0.5×PBS (pH 7.2) was added to tubes containing the final pellet. Following a 4-hr fixation, pellets were washed 3 times in 0.1 M sodium cacodylate buffer (pH 7.4) and postfixed in 1% osmium tetroxide in the same buffer for 1 hr at room temperature. The pellet was washed 3 times in a 4.5% aqueous sucrose solution and en bloc stained in an aqueous solution containing 1% uranyl acetate and 4.5% sucrose. The pellets were dehydrated in a series of graded ethanols followed by propylene oxide, infiltrated overnight with a 1:1 mixture of propylene oxide and LX-112 epoxy resin (Ladd Research, Burlington, Vt.), embedded in Beem capsules with pure LX-112 epoxy resin, and cured for 48 hr at 60° C. 60- to 70-nm thin sections were made with an Ultracut E microtome (Leica) fitted with a diamond knife (Diatome), mounted on naked 300-mesh copper grids, double stained with uranyl acetate and lead citrate in an LKB Ultrostainer (Leica), and stabilized by carbon evaporation in a vacuum evaporator (Denton Vacuum). Stained sections were observed and photographed with a Hitachi H-7000 electron microscope operated at 75 kV.

8. Postembedding labeling

For postembedding labeling, $1 \times 10^7$ cells were pelleted at 150×g the supernatant was removed, and the pellet was fixed with a freshly prepared buffered solution containing 4% formaldehyde, 0.1% glutaraldehyde, PBS (pH 7.2) for 2 hr at 4° C. All subsequent embedding procedures until dehydration were carried out at 4° C. to minimize antigen denaturation. The fixed cells were rinsed for 30 min with several changes of PBS containing 4.5% sucrose and treated for 1 hr with 50 mM ammonium in PBS to reduce free aldehyde groups. Cell pellets were washed with PBS, dehydrated in graded ethanols, and infiltrated successively for 1 hr each with a 1:1 and 1:2 mixture of absolute ethanol and LR Gold resin (Ted Pella, Inc.) followed by pure LR Gold resin and initiator (0.5% w/v benzoic methyl ether) overnight at 4° C. The cell pellets were transferred to and embedded in Beem capsules containing pure LR Gold resin and initiator and allowed to polymerize under UV light in a −20° C. cryochamber (Ted Pella) overnight. 60- to 70-nm thin sections were cut and mounted on naked 300-mesh nickel grids (Ted Pella). For immunolabeling, the grids were placed in a 50-slot Pellco grid storage box (Ted Pella), which permits 14 µl of labeling solution to be applied; all reactions were carried out at room temperature with the grid box in a moist chamber to avoid air drying. Grids containing sections were incubated in TTBS wash buffer, which consisted of a 1:10 dilution of normal serum in Tris-buffered saline (50 mM Tris, pH 8.2. 0.25 M sodium chloride, 0.1% BSA) containing 0.05% Tween-20, for 30 min. The Tween-20 and sodium chloride in TTBS wash buffer were added to block nonspecific attachment of primary (or secondary) immunoglobins and to facilitate removal of nonspecifically bound antibody or marker. The normal serum in TTBS was matched to the species used as the secondary antibody. Concentrations of these two reagents can be adjusted after preliminary results are obtained (i.e., increase or decrease concentrations if background is too high or weak signal is observed, respectively). After the blocking steps, the grids were rinsed with TTBS, incubated with a 1:20 dilution of primary antisera in TTBS for 2 hr, and washed in 3 changes Of TTBS buffer for 2 hr. The grids were then incubated in a 1:100 dilution of colloidal gold secondary antibody (discussed below) in TBS for 1 hr, and washed in TTBS buffer followed by a brief wash in distilled water. For washing, the grids are placed in a flexible grid holder used in the LKB ultrostainer and submerged in a 100 mm Petri dish containing wash buffer; the duration of washing steps has to be empirically determined, but usually is 1 hr with gentle agitation on a rocking platform. Immunolabeled thin sections were counterstained with uranyl acetate and lead citrate, stabilized, observed, and photographed, as described above.

B. Results
1. Morphogenesis of HIV

The morphogenesis of HIV reflects its relationship to the lentivirus genus of retroviruses (Gonda, M. A., *Ann. N.Y. Acad. Sci.,* 724:22–42 (1994); Gonda, et al., *Science,* 27:173–177 (1985)). An ultrastructural comparison of the various stages of maturation of HIV produced in human CD4+ lymphocytes was performed. In HIV, there was no intracellular form of the virus as seen with some other retroviruses (Gonda, et al., *Arch. AIDS Res.,* 3:1–42 (1989); Coffin, J. M., *The Retroviridae,* Vol. I (Levy, *J. A., Ed.), pp.* 19–49, Plenum Press (1992)). HIV particle formation began with the appearance of an electron-dense, crescent-shaped nucleoid, or core, beneath the plasma membrane of the infected cell. The nucleoid consists of Gag precursor, Pr55, which continues to accumulate and assemble beneath an envelope-studded plasma membrane. How the Gag precursor targets envelope-rich areas of the plasma membrane was not previously well understood. Morphogenesis continues until the immature extracellular virion, in the shape of a hollow sphere, buds from the cell membrane. Immature extracellular virions undergo maturation in which Gag and Gag-Pol polyproteins are processed by the viral protease; this alters the appearance of the immature extracellular virus and results in a condensation of the electron-dense core. In longitudinal section, the condensed core resembles a cone or rod and, in cross-section, a small circle with a variable electrondense center.

2. Expression of HIV Gag by Recombinant Baculoviruses in Insect Cells

Sf-9 cells were infected with AcMNPV-Hgag and examined by electron microscopy 3 days postinfection. Many HIV Gag pseudovirions were observed budding from the plasma membrane and cytoplasmic vacuoles and were found in the extracellular spaces. In addition, clusters of baculovirus were apparent in the nucleus. HIV pseudovirions resembled immature virus particles seen in thin-section analysis of HIV-infected H9 cells. As expected, no pseudovirions were observed with the morphology of mature virus, since sequences encoding the viral protease were not included in the constructs.

3. Electron Microscopy and Immunoblotting of Chimeric HIV Gag+Env Pseudovirions Produced in Insect Cells HIV Pr55 and gp160 were co-expressed from independent recombinant baculoviruses to determine the effect of gp160 on Gag particle formation. By election microscopy, immature virus-like particles were observed budding and free in the intercellular spaces. There was no morphological difference in the ultrastructure of Gag pseudovirions made in the absence or presence of gp160. By electron microscopy, it was not possible to determine whether the Gag pseudovirions incorporated Env into their lipid bilayer.

Western blot analysis of lysates from AcMNPV-Henv infected Sf-9 cells demonstrated that the HIV Env glycoprotein was expressed. The recombinant HIV gp160 was not cleaved into gp120 and gp41 functional subunits and, thus, migrated in denaturing gel electrophoresis as a 140-kDa protein. This is consistent with previous studies on the overexpression of the HIV gp160 in insect cells (Wells, et al., *Virology,* 176:575–586 (1990); Hu, et al., *J. Virol.,* 61:3617–3620 (1987)).

To further investigate whether HIV gp160 was incorporated into Gag pseudovirions, supernatant particles from co-infections of AcMNPV-Hgag and -Henv were analyzed by immunoblotting. Both HIV Gag and Env precursors were found in crude preparations of the pseudovirions, suggesting an association between these two proteins. However, gp160 could not be detected in Western blots of pseudovirions that had been detected to more rigorous purificationsTheThese results suggested that gp160 was only loosely associ or co-purified with Gag pseudovirions. Moreover, it could not be determined whether gp160 was oriented to the outside of the virus-like particles or was passively taken up during morphogenesis.

4. IEM of HIV Produced in Human Lymphocytes

To identify an association of gp160 with Gag pseudovirions, IEM was used. Two complementary techniques, indirect cell-surface labeling of infected cells prior to embedding and indirect labeling of postembedded samples were employed. As a first step in these experiments, several polyclonal and monoclonal antibodies to HIV Gag and Env (Table 1, supra) were characterized on HIV-infected H9 cells under a variety of concentrations and washing conditions in both indirect live cell-surface labeling and postembedding IEM methods. Colloidal gold-conjugated secondary antibodies were used as the marker of the microprecipitation reaction in these experiments. Live cell labeling of HIV-infected H9 cells with rabbit anti-HIV Pr55 Gag antibodies resulted in no labeling of virus particles or the infected cell surface. A similar pattern of negative reactivity was found for all of the additional polyclonal and monoclonal Gag antibodies found in Table 1, supra, (D3D9, P1F5, and anti-p24; data not shown). In contrast, labeling with all monoclonal and polyclonal anti-HIV gp120 antibodies demonstrated reactivity to HIV epitopes on the outside of the virus; albeit, the intensity of reactivity varied greatly between antibodies. Labeling with 3A3H3 monoclonal and anti-HIV gp120 antibody resulted in the deposition of numerous colloidal gold particles on the surface of budding and extracellular HIV virions. Occasionally, colloidal gold was observed on the infected cell surface; however, the reactivity was primarily confined to the site of budding. In all cases, the positive reactivity of anti-HIV gp120 antibodies by IEM were highly specific as no reactivity was observed with noninfected H9 cells.

Postembedding labeling of HIV-infected H9 cells with anti-Gag and -Env antibodies contrasted sharply with the live cell labeling. First, only the anti-Gag antibodies (anti-Pr55, anti-p24, D3D9, and P1F5) showed appreciable reactivity with budding and extracellular virus. The Env antibodies were rarely reactive with budding or free virions. Second, the reactivity with Gag and Env epitopes was weak even with low dilutions of primary antibody (1:10 to 1:120). Finally, the ultrastructural detail of virus particles was less well preserved than with the live cell labeling technique, making it difficult to clearly discern structural features.

5. IEM of HIV Gag and Chimeric Gag+Env Pseudovirions Produced in Insect Cells

Monoclonal antibodies or polyvalent antisera to HIV Gag and Env that were to have the strongest reactivity to target antigens in IEM of HIV-infected H9 cells were used to perform live cell-surface and postembedding labeling on HIV Gag and chimeric Gag+Env pseudovirions. In live cell-surface labeling, goat anti-HIV gp120 serum (G517) stained the outside of chimeric Gag pseudovirions produced from cells co-infected with AcMNPV-Hgag and -Henv on both budding and free extracellular particles. Various mouse monoclonal antibodies to HIV Env also shined the outside of the chimeric Gag+Env pseudovirions, but the reaction was weaker. Stronger reactivity was seen when monoclonal antibodies P8A9 and 3A3H3 were mixed (final dilution of 1:30 for each) (data not shown). Goat (G517) and mouse monoclonal antibodies (P8A9 and 3A3H3) to gp120 did not stain Gag pseudovirions produced from cells infected with AcMNPV-Hgag alone. Interestingly, by IEM, the appearance of recombinant gp160 on Sf-9 cells co-infected with AcMNPV-Hgag and -Henv correlated with areas of virus budding as observed with HIV-infected H9 cells. There was no labeling by IEM in live cell studies with any Gag antisera listed in Table 1, supra. Negative results were obtained with the rabbit anti-HIV Pr55 Gag serum with Gag or chimeric Gag+Env pseudovirions.

In postembedding labeling of thin sections of HIV pseudovirions, the monoclonal anti-HIV gp120 antibody (P3F5) reacted with chimeric Gag+Env pseudovirions produced from the co-infection of Sf-9 cells with AcMNPV-Hgag and -Henv, but not with Gag pseudovirions produced from infection of cells with AcMNPV-Hgag alone. The rabbit anti-HIV Pr55 serum reacted with pseudovirions produced by either type of infection.

C. Discussion

Recombinant baculovirus-insect cell expression systems have been used to produce large amounts of recombinant proteins for a wide variety of applications including synthesis of immunogens for antibody production, vaccination, biologically active cytokines, viral proteins for structure-function studies, and toxins for use as insecticides (Miller, L. K., *Curr. Opin. Genet. Dev.*, 3:97–101 (1993); Fraser, M. J., *Curr. Top. Microbiol. Immunol.*, 158:131–172 (1992); Wood, et al., *Annu. Re. Microbial.*, 45:69–87, 20 (1991); Maeda, S., *Annu. Rev. Entomol.*, 34:351–372 (1989)). This expression system has several features advantageous for the overproduction of HIV proteins and their assembly into pseudovirions. The system does not need the regulatory proteins necessary to express HIV proteins in mammalian cells (mRNA splicing, posttranslational fatty acid modification, glycosylation, and phosphorylation). Expression of Gag precursor proteins (Gonda, et al., *Control of Virus Diseases* (Kurstak, E., Ed.), pp. 3–31 (1992); Hu, et al., *J. Virol.*, 61:3617–3620 (1987)), and insect cells results in the budding of large numbers of pseudovirions that resemble immature HIV virions. The particles lack the viral genome or pol gene products, and thus are noninfectious. Gag pseudovirions retain many of the physical properties of naive virus and can be easily produced in substantially pure form using conventional virologic techniques.

The recent development of Gag pseudovirion technology forms the foundation for preparing more complex particulate vaccines for HIV. In the present study, recombinant baculoviruses were gene engineered to express HIV Pr55 or gp160 and used these baculoviruses to co-infect insect cells to produce noninfectious Gag pseudovirions that incorporate gp160 on the surface of the particle. The chimeric Gag pseudovirions made from the co-infection of insect cells with Gag and Env expressing baculoviruses are morphologically indistinguishable from pseudovirions made from baculoviruses that express Gag alone. Immunoblotting of crude preparations of pseudovirions produced by the co-infection of Gag- and Env-expressing baculoviruses demonstrated that gp160 was contained in these pseudovirions. However, it was unclear whether the gp160 that co-purified with crude preparation was randomly incorporated during budding or was actively recruited into pseudovirions during the budding process by an interaction between Gag and Env. IEM suggested that the latter was the case, as gp160 was primarily concentrated over areas of Pr55 assembly, suggesting a specific interaction between these two proteins. The association of gp160 with Gag precursor appeared to be unstable since gp160 was easily shed during more rigorous purifications of the pseudovirions.

IEM was chosen to determine the distribution of HIV gp160 as no other method currently is available to demonstrate the specific association and location of envelope proteins such as gp160 on the chimeric Gag pseudovirions and infected cells (reviEdsd in Gonda, M. A., *Immunochemistry* (van Oss, et al., Eds.), pp. 867–902 (1994); Gelderblom, et al., *Virology*, 156:171–176 (1987)). Indirect IEM was useful as it permitted the amplification of the primary microprecipitate. Colloidal gold-conjugated antibody markers were used in indirect IEM to identify the reaction between primary antibody and target antigen because of their electron density and versatility. Colloidal gold was seen even when electron-dense stains (e.g., uranyl acetate and lead citrate) were applied to sections. The colloidal gold particle was synthesized in various sizes and conjugated to affinity-purified antibodies of different specificities so that multiple antigens were detected simultaneously. Gold particle size was chosen based upon the size of the target structure (e.g., large gold conjugates for cellular antigens or membrane reactions and small gold conjugates for viruses). Colloidal gold conjugates of various sizes and with a wide variety of immunoglobin species specificities are commercially available. Colloidal gold IEM detection methods can be visualized with a silver enhancement step following the application of colloidal gold-conjugated secondary antibody (Holgate, et al., *J. Histochem. Cytochem.*, 31:938–944 (1983)).

Indirect IEM was used with both live cell-surface and postembedding labeling as these techniques address different questions and provide complementary information. In this example, live cell-surface labeling permitted the identification of HIV gp160 on the exterior of budding and extracellular pseudovirions and virions and its distribution on the recombinant baculovirus-infected and HIV-infected H9 cell surfaces, respectively. Cell-surface labeling methods are limited to the localization to proteins that appear on the outside of the cell surface membrane since antibodies cannot penetrate the cell membrane or viral envelope to reveal antigens embedded to the interior (e.g., Gag or Pol). Thus, for retroviruses, such as HIV, reactivity is primarily with envelope proteins. Native antigenicity is retained since no fixation or denaturation step is needed prior to the primary labeling. Ultrastructural detail is also better preserved than with most postembedding studies as long as isotonic buffers of a neutral pH are used in the numerous incubations and washes.

Postembedding IEM on thin sections enables the localization of antigens both on the cell surface and beneath the plasma membrane that are not readily available to cell-surface labeling techniques. Postembedding labeling demonstrated that HIV Gag proteins were found to the interior of the virions. Elegant studies effectively have used postembedding labeling on thin sections (Gonda, M. A., *Immunochemistry* (van Oss, et al., Eds.), pp. 867–902, (1994); Gelderblom, et al., *Virology*, 156:171–176 (1987)). However, obtaining results with postembedding labeling requires more rigorous technical manipulations to optimize detection of antigen that does cell-surface labeling. A few technical considerations that may affect obtaining successful staining results are given below. First and foremost, the sensitivity of detection of some antigens is reduced to fixation, dehydration with alcohols, and embedding in a resin (i.e., the epitopes may be denatured, cross-linked, and masked with resin). Thus, antigen concentration and sensitivity to denaturation and crosslinking may play more important roles in the postembedding technique. Therefore, it is advantageous to use a high-titered polyclonal antibody or a mixture of distinct monoclonal antibodies to overcome the lack of antigen availability or reactivity. If negative results in IEM are obtained with a single antibody of proven reactivity in other immunological assays (e.g., Western blots and radioimmunoprecipitations), additional antibodies or different fixatives should be evaluated. Secondly, the image quality (and antigen availability) is not as good in postembedding labeling as with the live cell-surface labeling techniques. This is partially due to the use of gentle fixatives required to preserve antigenicity at the expense of ultrastructural morphology. Virus particles are very susceptible to morphologic detail loss in the postembedding method. To overcome these obstacles, new embedding resins have been developed (LR White and LR Gold) that have improved both antigen availability and image quality in postembedding labeling. However, there is still room for improvement. Finally, while postembedding techniques permit the detection of intracellular antigens, the resolution of the reaction is limited to the size of the antibody-gold conjugates at the microprecipitate (~15 to 30 nm). In the case of HIV virions, which are 120 nm in diameter, the precise localization of Gag or Env antigen as being to the inside or outside of the particle would be very difficult to ascertain in postembedding label IEM. Thus, the location of the gold particle in postembedding IEM is an approximation of the location of the epitope, and statistical analysis of the position of the particles relative to specific morphological features must be used to derive a more precise location of the epitope.

Example 2
Strategies for Packaging Additional HIV Viral Epitopes

Using the particle forming properties of the HIV Gag precursor (Pr55) as the foundation for these studies, three strategies for packaging additional HIV viral epitopes or cellular polypeptides into Gag pseudovirions were evaluated. In the first, insect cells are co-infected with recombinant baculoviruses expressing either Gag or Env precursors (Tobin, et al., *ImmunoMethods* (in press); Example 1). In the second, sequences encoding short Env epitopes are inserted at the 3' end of the Gag p6 domain for expression as chimeric inframe Gag-fusion proteins. In the third, sequences encoding a large fragment of SU are inserted into the Pol reading frame 3' of the Gag stop codon. In the latter strategy, the possibility of utilizing the natural frameshifting mechanism of the lentivirus Gag-Pol translation to make chimeric Gag-frameshift(fs)-fusion proteins was investigated. In the foregoing strategies, the ability of recombinant Gag and Env precursors or chimeric Gag-fusion proteins to assemble into pseudovirions in insect cells was evaluated by transmission electron microscopy, immunoelectron microscopy (IEM), and Western blot analysis.

A. Gag Pseudovirions

Sequences encoding the entire Gag precursor proteins of a variety of lentiviruses have been cloned behind the strong baculovirus polyhedron promotor in baculovirus transfer plasmids, incorporated into recombinant baculoviruses, and used to successfully make pseudovirions in insect cells (Madisen, et al.; Cheysen, et al.; Delchambre, et al.; Rasmussen, et al.; Morikawa, et al.; Wagner, et al.; Tobin, et al., all supra). As an example, FIGS. 1A shows the gene structure and predicted translation of HIV gag in a baculovirus transfer plasmid. The transfer plasmids were co-transfected with AcNMPV DNA into Sf-9 insect cells and recombinant baculoviruses were isolated using standard methodologies (Tobin, et al., supra; Summers, et al., suipra). Expression of HIV Gag precursor proteins by the recombinant baculovirus results in their assembly into budding particles beneath the plasma membrane and the secretion of large quantities (1–10 mg/L culture supernatant) of virus-like particles. Because sequences encoding the retroviral protease were omitted from the HIV sequences expressed by the recombinant baculovirus, the pseudovirions were composed of unprocessed Gag precursor proteins and resembled immature HIV virions (see also, Gonda, et al., *Science,* 227:173–177 (1985)). Gag pseudovirions were purified readily from the culture supernatant by standard virologic techniques that included polyethylene glycol precipitation (PEG) and sucrose gradient sedimentation (Cheysen, et al.; Rasmussen, et al.; Tobin, et al., all supra).

B. Co-expression of Gag and Env Precursors

The HIV Env glycoproteins contain many immunologically and functionally important domains of the virus (Ratto, et al., *J. Infect. Dis.,* 171:1420–1430 (1995)). The most straightforward approach to incorporate Env epitopes into Gag pseudovirions was to co-express Gag and Env precursors in insect cells and allow them to naturally associate at the insect cell plasma membrane. The $HIV_{MN}$ strain was chosen as the donor of env sequences as it is a prevalent North American serotype, and widely available. Sequences encoding the entire SU and transmembrane (TM) domains of the env gene were cloned into a baculovirus transfer plasmid behind the polyhedron promoter to make a recombinant baculovirus (FIG. 1B). Previous reports indicated that the recombinant HIV Env precursor was glycosylated, but not cleaved into SU and TM subunits in insect cells and, thus migrates in sodium dodecyl sulfate-polyacrylamide gel electrophoresis with an apparent molecular mass of 140 kDa. Western blot analysis of lysates made from insect cells infected by the recombinant baculovirus expressing HIVMN Env confirmed the presence of a recombinant HIV Env precursor of 140 kDa as predicted (Hu, et al., supra; Wells, et al., supra).

To co-express both Gag and Env precursors, recombinant baculoviruses encoding Gag or Env were used in a 1:1 ratio to co-infect insect cells. Electron microscopic analysis demonstrated that pseudovirions were produced. IEM was used to determine whether Env was incorporated into the pseudovirions. Live cell surface- and postembedding-labeling IEM methods were used with either a mouse monoclonal anti-HIV gp120 antibody or a rabbit anti-HIV p24 serum. Colloidal gold-conjugated goat anti-mouse or -rabbit IgG secondary antibodies were used to detect bound primary antibodies, according to described methods (Tobin, et al., *ImmunoMethods* (in press); Gonda, M. A., *Immunochemistry* (van Oss, et al., eds.) New York, Marcel Dekker, pp. 867–902 (1994). In live cell surface-labeling JEM, gp120 was detected an the envelope of pseudovirions budding from insect cells co-expressing Gag and Env, but not on those budding from insect cells expressing Gag alone (negative control). In postembedding IEM, this sections were made and stained with antibody to HIV gp120 or p24. Gag was detected on all pseudovirions whereas Env was detected only on pseudovirions produced from the cells co-infected with baculoviruses that expressed Gag and Env.

Retroviruses are known to shed their surface glycoproteins upon purification. To examine if the pseudovirions retained the Env protein after purification, crude and purified particle preparations from culture supernatants of co-infected insect cells were assayed for Env by Western blotting. Four days after infection, Gag+Env-containing particles were purified from the culture supernatant of co-infected cells. Crude preparations (i.e., particles pelleted through 10% (w/w) sucrose) contained material reactive with anti-gp120 antibodies. PEG precipitation of supernatants also contained HIV Env. However, when the particles were purified by PEG precipitation followed by sedimentation in 10 to 60% (w/w) sucrose gradients, little or no Env could be detected by Western blotting. The Gag precursor, Pr55, was detected by a monoclonal antibody to HIV p17 at all stages of purification.

C. Inframe Gag-fusion Proteins

Since the HIV Env protein was shed easily from the outside of the particle, the linking of Env epitopes, or other molecules, directly to the HIV Gag precursor as inframe Gag-fusion proteins for expression by recombinant baculoviruses was studied. A series of recombinant baculoviruses was engineered to overexpress inframe HIV Gag-fusion proteins by cloning sequences encoding the PND, CD4Rc, or PFD of the HIV Env glycoprotein behind the 3' end of the HIV Gag p6 domain, with expression being given by the strong polyhedron promoter. To assess the packaging efficiency of larger fusion partners, analogous constructs were made to package human IL-2.

Insect cells infected with baculoviruses that encode inframe HIV Gag-fusion proteins were examined by electron microscopy for pseudovirion production. Although expression of the chimeric HIV Gag-PND and HIV Gag-PFD proteins could be demonstrated by Western blotting lysates of recombinant baculovirus infected cells, no budding or extracellular particles were observed by electron microscopy. Instead, there was an accumulation of chimeric Gag fusion protein beneath the plasma membrane indicative of an early block in particle morphogenesis. In contrast, cells infected with the baculovirus expressing Gag-CD4Rc produced a large quantity of pseudovirions comparable to cells infected with baculoviruses expressing Gag alone. In cells infected with a recombinant baculovirus that expressed HIV Gag-IL2, only a few rare extracellular particles could be found; most of the overexpressed chimeric Gag protein appeared to accumulate at the plasma membrane without budding.

The relative quantities of pseudovirions produced by cells infected with these recombinant baculoviruses and expressing inframe Gag-fusion protein were examined by gel electrophoresis. Pseudovirions were purified and concentrated from equivalent volumes of supernatants of 4-day-postinfection cultures by PEG precipitation followed by sedimentation through 30% sucrose. Supernatants from cultures infected with baculoviruses that expressed HIV Gag or Gag-CD4Rc contained large quantities of Gag-related proteins that could be detected readily by Coomassie staining and Western blotting. In contrast, expression of HIV Gag-PND, -PFD, or Gag-IL2 resulted in little or no detection of Gag-related proteins in the supernatant.

D. Gag-fs-fusion Proteins

In mammalian cells infected with lentiviruses, the Gag and Gag-Pol precursor proteins are both translated from the full-length viral mRNA. Most translations terminate at the Gag stop codon. However, in approximately 5% of the translations, the ribosome undergoes a −1 frameshift that results in a shift from the Gag reading frame to the Pol reading frame (Jacks, et al.; Varmus, H.; Battles, et al., all supra). In this embodiment, the HIV frameshifting mechanism was utilized to package additional epitopes inside the core of the pseudovirion. Sequences encoding the carboxyl 65% of the $HIV_{MN}$ gp120 were cloned into the HIV pol reading frame, 3' of the Gag stop codon and 5' of the protease active site, in a baculovirus transfer plasmid that was used to engineer a recombinant baculovirus.

Insect cells infected with recombinant baculoviruses designed to express HIV Gag-fs-SU were examined for pseudovirion formation by electron microscopy. Many budding and extracellular pseudovirions were observed, and the quantity of particles produced from baculoviruses expressing the frameshift proteins was equivalent to that made from baculoviruses expressing the Gag precursor only. The packaging of additional polypeptides did not alter the ultrastructural morphology of the pseudovirions. In addition, Env epitopes were observed inside the HIV Gag-fs-SU pseudovirions by IEM, and chimeric Gag-SU proteins could be detected in Western blots of purified particles using a monoclonal mouse anti-gp120 antibody.

E. Discussion

The native retrovirus can morphologically be divided into two major components: the envelope and core (Levy, J. A., supra; Gonda, et al., *Control of Virus Diseases* (Kurstak, E., ed.), New York, Marcel Dekker, pp. 3–31 (1992)). There is an immune response to both components in HIV infections. Thus, it is important to include both Env and Gag proteins in Hrecombinant, noninferecombinant, noninfectious particulate class, such as the pseudovirions described herein. The above experiments have determined how these components can structurally be maintained in association with each other in the baculovirus insect cell expression system. Some lentiviruses appear to hold onto their Env glycoproteins more firmly than others. In contrast, gp120 is easily shed from many HIV laboratory strains, including $HIV_{MN}$. The above results in the baculovirus system indicate that the production of HIV Gag pseudovirions adorned by Env, through co-infection of insect cells with recombinant baculoviruses expressing Gag and Env precursors separately, is technically feasible. However, retention of Env on the surface of these particles during purification steps remains problematic. This may be related to properties of HIV gp120, or as yet unidentified cellular or viral cofactors needed to stabilize the pseudovirion envelope in insect cell's.

The native virion is capable of packaging additional macromolecules including the Gag-Pol precursor and the viral RNA. This suggested to us that we could get assembly of pseudovirions in which additional polypeptides were packaged to the interior. The above results demonstrate pseudovirion production in insect cells with chimeric inframe Gag-fusion proteins in which the fusion partners were HIV Env polypeptides inserted in the Gag open reading frame behind p6. Other laboratories have reported similar successes in the production of chimeric HIV Gag pseudovirions in which the HIV polypeptides were expressed in frame with Gag intragenic regions (Luo, et al., *Proc. Natl. Acad. Sci. USA,* 89:10527–10531 (1992); Wagner, et al., *Virology,* 200:162–175 (1994); Wang, et al., *Virology,* 200:524–534 (1994); Griffiths, et al., *J. Virol.,* 67:3191–3198 (1993)). The results from our laboratory suggested that certain combinations of Gag and fusion partner were detrimental to particle assembly. This seemed to be the case even with the small peptide (53 residues) representing the PND. While it is not known which sequences were responsible, it is thought that the cysteine residues in the PND may interact with nucleocapsid protein sequences, also rich in cysteine residues, thus disrupting Pr55 association. Other studies (Morikawa, et al., supra; Luo, et al., supra; Wagner, et al. *Virology,* 200:162–175 (1994); Wang, et al., *Virology,* 200:524–534 (1994); Griffiths, et al., supra; von Poblotzki, et al., *Virology,* 193:981–985 (1993); Hong, et al., *J. Virol.,* 67:2787–2798 (1993)) have found that the location of the insertion within the Gag precursor can dramatically affect the formation of chimeric Gag particles. In addition to composition and position, the presence of additional peptides may sterically hinder assembly of chimeric Gag proteins into budding pseudovirions.

Alternatives to the inframe Gag-fusion-protein strategy were considered in packaging Env epitopes to the interior of the particle. In doing so, the possibility of utilizing the natural gag-pol frameshifting mechanism of lentiviruses to coordinate the inclusion of additional polypeptides into pseudovirions was investigated. Thus, the construct designed to express the Gag-fs-SU included sequences identified to be important in ribosomal frameshifting (Jacks, et al.; Varmus, H.; Parkin, et al., all supra). Without intending to be bound to any theory, it is thought that translational control may be advantageous to virus assembly as it naturally facilitates the correct expression, concentration and, thus, packaging of non-Gag polypeptides such as Pol in Gag-Pol polyproteins. Quite surprisingly, this strategy was successfully applied to the packaging of HIV Env SU epitopes into Gag particles.

The inoculation of Gag pseudovirions into mice, rabbits, and macaques results in strong humoral and cellular immune responses that do not require the use of adjuvants (Wagner, et al., supra; Tobin, et al., *Methods in Molecular Genetics, Molecular Virology* (Adolph, K. W., ed.), Orlando, Academic Press, in press, vol. 4). The immune response of mice inoculated with Gag-fs-SU pseudovirions was evaluated and, interestingly, while the Gag component of pseudovirions induces strong humoral and CTL responses, the SU component of Gag-fs-SU pseudovirions elicits only a strong CTL response. Thus, the present results demonstrate a novel role for chimeric Gag-fs-SU pseudovirions produced in the baculovirus insect cell system as vaccines and postinfection therapies as described above.

Example 3

Insect Cell Expression of HIV-1 Gag Pseudovirions Containing gp120 Domains

In this example, insect cell expression of the HIV-1 Gag precursor protein by recombinant baculoviruses results in the assembly and budding of noninfectious virus-like particles (VLPs). The VLPs resemble immature virus in ultrastructural morphology and can be purified by conventional retroviral techniques. The virus-like appearance of the particles suggested that they could be used to package additional peptides. The retroviral frameshift mechanism was used to translate the pol gene products by expressing additional genetic information as chimeric Gag-Pol fusion proteins. Sequences encoding the carboxyl 65% of the HIV-1 surface glycoprotein (gp120, SU) were inserted into the Gag-Pol reading frame immediately downstream of the Gag stop codon. The assembly and budding of large quantities of Gag and chimeric Gag-SU VLPs were observed by standard transmission electron microscopy. The presence of gp120 epitopes in the Gag-SU VLPs were confirmed by immunoelectron microscopy and Western blot analysis using monoclonal anti-gp120 antibodies. Mice inoculated with the Gag-SU pseudovirions developed cytotoxic lymphocyte responses to both HIV-1 Gag and Env epitopes yet humoral immune responses only to Gag epitopes. The chimeric Gag-SU particles may have applications as vaccines or immunotherapeutic treatments for HIV-1 infection. In addition, as explained throughout the specification, the frameshift mechanism can be applied to the packaging of other viral or cellular proteins.

A. Materials and Methods

1. Genetic engineering of recombinant baculoviruses

Generation of the recombinant baculovirus that directs the expression of the HIV-1 gag gene (AcMNPV-Hgag) has been described (Tobin, G. J., et al., *Intervirology* 39, 40–48 (1996)). For the generation of AcMNPV-Hgag-SU, DNA sequences encoding the entire HIV-1 hxb2 Gag precursor were amplified from pHXB2 (Ratner, L., et al., *AIDS Res. Hum. Retroviruses* 3, 57–69 (1987)) using the polymerase chain reaction with primers 5'ACTAGCGGAGGCTA-GAAGGAGAGAG (nt 765 to 789) (SEQ ID NO: 5) and 5'GTTTAAACGTTAACTTAATTACTTGC-TACGCGTTAGAGCTTCC TTTAGTTGCCCCCC (nt 2297 to 2320) (SEQ ID NO: 6). The reverse oligo encoded restriction endonuclease (RE) sites Mlul, Pacl, Hpal, and Pmel to facilitate successive sequence insertions.

Sequences encoding the carboxy 65% of HIV-1 mn gp120 and the first 14 residues of the transmembrane glycoproteins were amplified from pHIV-1 mn-st1 (see, e.g., Lori, F., et al. (1992) *J. Virol* 66, 5553–5560) with primers 5'CCGGT-TAATTAATGGAATTAGGCCAGTAGTATCAACT (nt 7000 to 7024, including a Pacl RE site and an additional nucleotide to put the SU portion inframe with Gag-Pol) (SEQ ID NO: 7) and 5' GCATGTTTAAACTGCTGCTC-CTAAGAACCCAAGGAA (nt 7796 to 7819, including a Pmel RE site) (SEQ ID NO: 8). The amplified fragments were cloned separately into pCRII (Invitrogen) to generate pCR-Hgag and pCR-HSU, respectively. All plasmids generated by PCR methods were confirmed by DNA sequence analysis. The SU fragment was excised from pCR-HSU by digestion with Pacl and Pmel and cloned into pCR-Hgag 3' of the Gag stop codon such that the SU codons were in the Gag-Pol reading frame. The Gag-SU cassette was excised with EcoRI and Pmel and cloned into the baculovirus transfer vector pBacPAK4 (Clonetech) to generate pBac-Hgag-SU. AcNMPV-Hgag-SU was derived by co-transfection of pBac-Hgag-SU and AcNMPV genomic DNA into Sf-9 cells using standard baculovirus technologies (Tobin, G. J., et al. (1995) *Methods in Molecular Genetics*, Vol. 7, Molecular Virology, K. W. Adolph, ed., Academic Press, Orlando, pp. 237–253; Summers, M. D., et al. (1987) Texas Agricultural Experiment Station Bulletin No. 1555, College Station, Tex., Texas Agricultural Experiment Station).

2. Insect cell culture and baculovirus infection

Spodoptera frugiperda Sf-9 insect cells were propagated in Graces's media supplemented with 7% fetal bovine serum (FBS) and 0.33% each of lactalbumin hydrolysate and yeastolate. For production of VLPS, cells were infected with recombinant baculoviruses at a multiplicity of infection of 5 plaque-forming units per cell.

3. Electron microscopy

At 2 days postinfection, cell cultures were removed from the flasks by gentle scraping, pelleted at 150 g for 5 min, and fixed and embedded for either standard transmission electron microscopy (TEM) or postembedding immunoelectron microscopy (IEM) as previously described (Tobin, G. J., et al. (1996) *Intervirology* 39, 40–48). For IEM, 60- to 70-nm thin sections were cut, mounted on a nickel grid, incubated in a 1:10 dilution of normal goat serum in 50 mM Tris-HCl, pH 8.2, 250 mM NaCl, and 0.1% BSA; and reacted with 1:20 dilutions of mouse monoclonal anti-p17 (D3D9) or antigp120 (P8A9) antibodies (obtained from Drs. S. Nigida and L. Arthur, AIDS Vaccine Program, NCI). The sections were washed, incubated in 1:100 dilutions of 10-nm colloidal gold-conjugated secondary antibody for 1 h, and re-washed. The thin sections were counterstained with uranyl acetate and lead citrate, stabilized by carbon evaporation, observed, and photographed with an Hitachi H-7000 electron microscope operated at 75 kv.

4. Purification and protein analysis of virus-like particles

Four days following infection, VLPs were purified from Sf-9 culture supernatants based upon their particulate nature and buoyant density as previously described (Gheysen, D., et al. (1989) *Cell* 59, 103–112; Rasmussen, L., et al. (1990) *Virology* 178, 435–451; Tobin, G.J., et al. (1995) *Methods in Molecular Genetics*, Vol. 7, Molecular Virology, K. W. Adolph, ed., Academic Press, Orlando, pp. 237–253). Briefly, culture supernatants were clarified at 2000 g for 15 min; precipitated in 2.3% NaCl and 8% (w/v) polyethylene glycol; resuspended in 10 mM Tris-HCI, pH 8.0, 1 mM EDTA, and 150 mM NaCl (TNE); and centrifuged through 10–60% (w/w) sucrose gradients in TNE for 3 h at 85,000 g. The material that sedimented at 1.16 g/ml was removed from the gradients, diluted in 3 volumes of TNE, repelleted for 1.5 h at 85,000 g, and resuspended in TNE. Total protein concentration of the purified material was estimated using the Bradford dye-binding method (Bio-Rad Laboratories, Inc.) and comparison to known concentrations of bovine serum albumin. Approximately 5 mg of purified VLPs were obtained from 1 L of insect cell culture supernatant.

Proteins contained within the VLP preparations were resolved on denaturing polyacrylamide gels and transferred, to PVDF membranes for immunoblotting using standard techniques (Coligan, J. E., et al. (1994) *Current Protocols in Immunology*, Vol. 1, Wiley-Interscience, New York). Immobilized proteins were reacted with 1:5000 dilutions of mouse monoclonal anti-p17 (D3D9) and anti-gp120 (P8A9), washed and reacted with horseradish peroxidase conjugated goat anti-mouse IgG antibody. Bound antibody was visualized by chemiluminescence (Amersham) and exposure to XAR-5 film (Kodak).

5. Immunization of mice

Two groups of female Balb/c mice, 6 to 8 weeks of age, were inoculated by subcutaneous injection of either HIV Gag or Gag-SU particles in two independent experiments. In Experiment 1, mice were inoculated with 20 μg VLPs suspended in 0.2 ml volume of either complete Freund's adjuvant or phosphate buffered saline (PBS). Boosts containing the same quantity of antigen were done at three-week intervals in either incomplete Freund's adjuvant or PBS, respectively. Serum samples were prepared from the mice at each inoculation. The spleens from approximately 50% of the mice were removed for analysis after four injections and the remainder of mice were processed after six injections. In Experiment 2, mice were injected once with either 2 or 20 μg VLPs in PBS. Three weeks after the final immunization of both experiments, serum samples were collected and spleens were removed for immunological assays.

6. Immunological assays

Serum samples from immunized mice were tested for HIV Gag and Env reactivity by standard immunoblot techniques (Coligan, J. E., et al. (1994) *Current Protocols in Immunology*, Vol. 1, Wiley-Interscience, New York). Briefly, either sucrose gradient-purified Gag VLPs or affinity-purified native gp120 (obtained from J. Bess and L. Arthur, AIDS Vaccine Program, NCI) was electrophoresed and transferred to PVDF membranes. The membranes were cut into 5 mm strips, reacted with mouse sera from inoculated animals diluted 1:500 (Gag strips) or 1:100 (gp120 strips), and alkaline phosphatase conjugated goat anti-mouse antibody diluted 1:5000 or 1:1000, respectively. Bound antibodies were visualized by chemiluminescence and autoradiography.

Splenic cells were assayed for cell-mediated lysis of P815 mastoblastoma cells infected with recombinant Gag or Env vaccinia viruses (obtained from P. Earl and B. Moss, NIH) as described (Walker, B. D., et al. (1987) *Nature* (London) 328, 345–8). Single cell suspensions of spleens were cultured for 5 days in RPMI media supplemented with 10% (v/v) FBS, 0.01% (w/v) purified Gag VLP, 0.001% (w/v) gp120, and 10 i.u./ml human IL-2 (Cetus) to propagate effector T cells. P815 cells were infected at an m.o.i. of 5 pfu/ml with either Gag-, or Env-vaccinia viruses 17 h prior to the start of the lysis assay. Effector and target cells were washed twice in chemically-defined, serum-free media (Opti-MEM, Life Technologies) at the start of the assay. Assays consisted of triplicate wells containing $1 \times 10^4$ target cells mixed with between $3 \times 10^4$ and $1 \times 10^6$ effector cells in a total volume of 0.2 ml Opti-MEM. Negative and positive lysis control wells contained no effector cells, and 0.1% Triton X-100, respectively. Four hours after the start of the assay, 0.1 ml culture supernatant was carefully withdrawn and the amount of lactose dehydrogenase was quantitated using an enzymatic tetrazolium-based assay read at 690 nm (LDH assay, Boehringer Mannheim Biochemicals). The mean absorbance values of the negative lysis controls were subtracted from the mean values of the triplicate experimental wells. The percent lysis was expressed as the ratio of the absorbance values of the subtracted experimental wells to the detergent lysed (total lysis) wells. Percent lysis data was graphed for individual mouse splenocyte cultures in Experiment 1 and for splenocyte pools in Experiment 2.

B. Results

1. Incorporation of gp120 epitopes in budding VLPs

Sf-9 cells infected with recombinant baculoviruses were examined by TEM and IEM. Standard TEM analysis of embedded cells which had been infected with either AcNMPV-Hgag or AcNMPC-Hgag-SU revealed large numbers of VLPs budding and budded from the plasma membrane. As per Example 1 (see also, Tobin et al. (1996) *Methods: A Companion to Methods in Enzymology* 10, 208–218, Gheysen, D., et al. (1989) *Cell* 59, 103–112), the hollow sphere appearance of the HIV Gag VLPs resembled immature lentivirus particles. The Gag and GagSU VLPs were indistinguishable from each other by conventional TEM. Consistent with the engineering of the SU to the carboxyl portion of the Gag precursor, no glycoprotein projections were seen on the surface of the VLPS.

For post-embedded IEM analysis, thin sections of insect cells infected with either AcNMPV-Hgag or AcNMPV-Hgag-SU were reacted with mouse anti-Gag and anti-SU monoclonal antibodies followed by colloidal gold-conjugated goat anti-mouse antibody. Labeling with anti-p17$^{Gag}$ antibody resulted in the deposition of numerous colloidal gold particles on the surface of budding and budded Gag and Gag-SU VLPs. In contrast, labeling with anti-gp120 antibody, resulted in the labeling of only the Gag-SU VLPs.

2. Chimeric VLPs package Gag-SU fusions

Based upon the DNA sequences of the baculovirus constructs, the molecular masses of the Gag and GagSU proteins were calculated to be approximately 55,930 and 89,208 daltons for the 500 and 798 residue proteins, respectively. Proteins contained in preparations of sucrose gradient-purified VLPs were resolved by denaturing PAGE and analyzed by Western blotting. Membrane strips containing 0.15 μg Gag or 1.5 μg GaarSU VLPs were reacted with anti-17$^{Gag}$ and anti-gp120 monoclonal antibodies. A protein species of approximately 55 kDa present in each VLP preparation was detected by the anti-p17$^{Gag}$, but not the anti-gp120 antibody (lanes 3 and 6). In contrast, both antibodies reacted with a protein of approximately 90 kDa present in the Gag-SU but not the Gag VLP sample (lanes 2, 3, 5, and 6).

3. VLPs elicit a humoral response to Gag but not Env epitopes

To study the humoral antigenicity of the HIV VLPS, female Balb/c mice were inoculated repeatedly with sucrose gradient-purified Gag and Gag-SU as described in Methods. Serum samples from the immunized mice were examined for reactivity to the HIV Gag precursor using Western blot strips containing 0.25 µg sucrose gradient-purified Gag VL. Sera, collected after the second Gag or Gag-SU VLP immunization reacted with Pr55$^{Gag}$ as did sera from later bleeds. The Gag reactivity of sera from mice inoculated with VLPs in PBS appeared similar to that of sera from mice inoculated with VLPs in Freund's adjuvant. Western blot strips containing 0.5 gg gp120 purified from HIV-1 infected human cells were used to test the generation of anti-SU antibodies in mice inoculated with Gag-SU VLPs. Serum samples that were drawn after multiple inoculations of Gag-SU VLPs failed to react to native gp120. The presence of adjuvant in the inocula did not affect stimulation of anti-gp120 antibodies.

4. Chimeric VLPs stimulate CTL responses to Gag and Env epitopes

Figure 2:
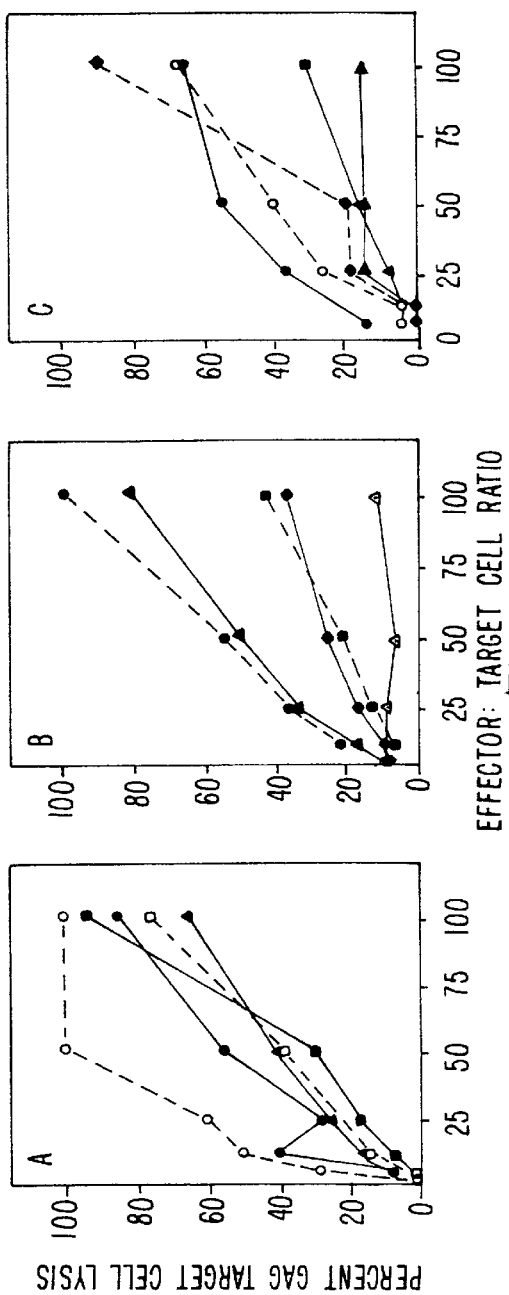

To study the stimulation of Gag and Env-specific cellular immune responses, female Balb/c mice were inoculated with sucrose gradient-purified VLPs in two independent experiments as described in Methods. Splenocytes from mice that received four injections of HIV Gag-SU VLPs were stimulated with antigen in vitro and assayed for lysis of P815 cells expressing HlVmn gpl 60 (FIG. 2). Lysis of target cells at varying effector:target cell ratios was expressed as the percent total target cell lysis by comparison to detergent-lysed control wells. Data points represented by open symbols and dashed line were derived from mice inoculated with Gag-SU in Freund's adjuvant; solid symbols and lines were derived from mice inoculated with Gag-SU in PBS. Each line in FIG. 2 represents the percent target cell lysis of an individual mouse. The lysis data in Panel A indicates that each mouse developed measurable Env-specific lysis and that the level of lysis was relatively high at 1:100 and 1:50 ratios regardless of the presence of adjuvant. Splenocytes from mice that received an additional two boosts of Gag-SU were assayed for lysis of Env and Gag targets six weeks later (FIGS. 2B and 2C). Although two mice appeared to generate anti-Env CTL responses comparable to those shown in Panel A, three mice exhibited weaker responses (FIG. 2B). Splenocytes from Gag VLP-inoculated mice lysed Gag targets efficiently at effector:target ratios of 50 and 100 (FIG. 2C). Splenocytes from Gag-SU inoculated mice showed a wide range of anti-Gag lysis as one culture lysed the targets well at high ratios while two others showed marginal activity. It should be noted that the splenocyte cultures that produced the lowest level of Gag and Env CTL activities in FIG. 2B and 2C. also had lower cell viabilities compared to the cultures that demonstrated higher CTL responses. The presence of Freund's adjuvant in the inocula did not appear to be a factor in the CTL activities that were generated.

Figure 3:
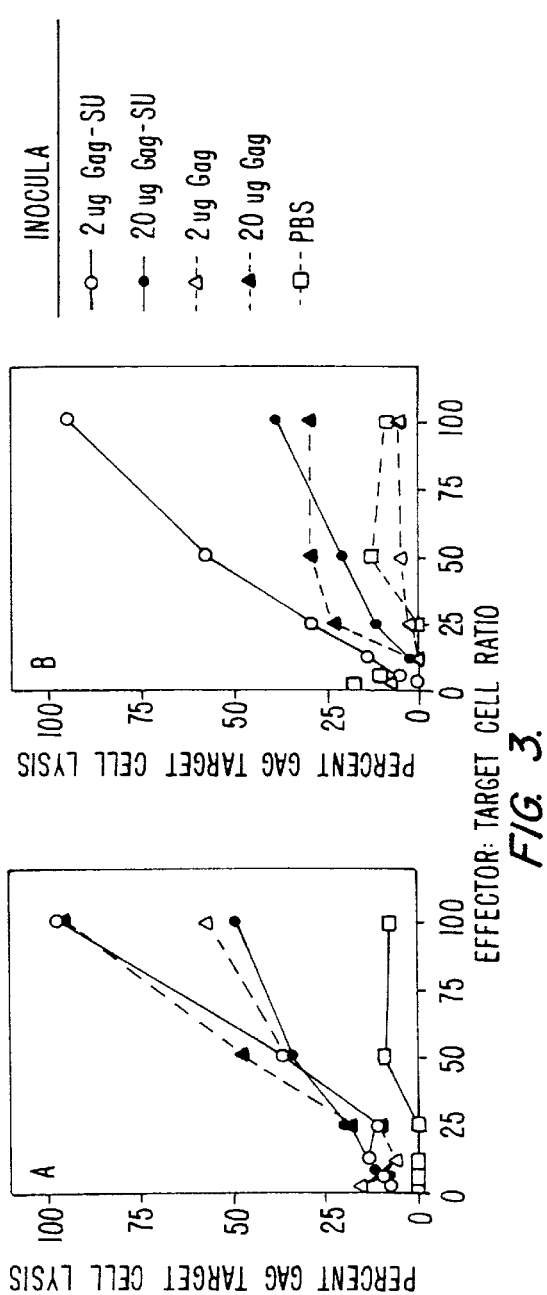

To assess the effect of VLP concentration on the generation of an HIV-specific CTL responses, four groups of four female Balb/c mice were inoculated once with either 2 or 20 µg of Gag or Gag-SU VLPs in 0.2 ml PBS. An additional group was inoculated with PBS as a negative control. Three weeks following the inoculation, splenocyte cultures from the five groups were pooled, stimulated in vitro, and tested for lysis of Gag and Env target cells. Splenocytes from mice immunized with Gag-SU VLPs lysed both Gag and Env targets (FIG. 3). The correlations between percent lysis and CTL effector:target cell ratios were approximately linear between ratios of 25 to 100. At the highest ratios, mice that were inoculated with 2 µg of antigen generated greater CTL activities than those inoculated with 20 µg. Splenocytes from mice inoculated with Gag VLPs demonstrated similar patterns of Gag-specific target lysis as those inoculated with Gag-SU (FIG. 3A). In addition, some apparently nonspecific cell lysis was observed from mice inoculated with 20 µg but not 2 µg Gag VLPs (FIG. 3B).

C. Discussion

The expression of the HIV Gag precursor protein in insect cells resulted in the assembly and budding of numerous VLPS. The co-expression of a large portion of the SU protein in the Gag-Pol reading frame resulted in the production of VLPs that packaged the Gag-SU fusion protein with Pr55$^{Gag}$. The presence of the SU fragment in the VLPs was confirmed by post-embedded IEM analysis of insect cells infected with AcNMPV-Hgag-SU. In addition, immunoblot analyses of purified Hgag-SU VLPs indicated that a protein of the predicted mobility for the Gag-SU fusion protein contained both Gag and SU epitopes. Although Western blots are semiquantitative at best, a comparison of the relative intensities of the Pr55 and the Gag-SU protein bands suggested that the ratio of the two proteins in the chimeric particles is approximately 1:100. This ratio is consistent with previously reported frequencies of translational frameshifting (Parkin, N. T. et al. (1992) J. Virol. 66, 5147–5151). In previous studies, relatively large fusion partners were expressed inframe at the C-terminus of the Gag precursor (Tobin, G. J. et al. (1996) Methods: A Companion to Methods in Enzymology 10, 208–218). Because these inframe fusion proteins failed to assemble and bud efficiently from the plasma membrane, it is likely that a reduced molar ratio of fusion protein to Gag precursor permits efficient particle formation and a large fusion partner on the C-terminus of each Gag precursor molecule may interfere with particle formation. Although other groups have constructed chimeric HIV Gag VLPs containing short, in-frame gp120 epitopes (Luo, L. et al. (1992) Proc. Natl. Acad. Sci. USA 89, 10527–10531; Wagner, R. et al. (1996) Virology 220, 128–140) frameshift fusion proteins appear to accept larger peptide insertions.

Multiple inoculation of mice with either Gag or Gag-SU VLPs resulted in strong humoral responses to Gag epitopes, but not to gp120 epitopes (FIG. 2B). In contrast, CTL responses to both Gag and SU epitopes were seen in mice given a single 2 µg inoculation of Gag-SU VLPs (FIG. 3). Previous reports have suggested that the inclusion of adjuvants in VLP inocula causes a shift toward a predominant humoral response and away from a CTL response (Layton, G. T. et al. (1993) J. Immunol. 151, 1097–1107; Wagner, R. et al. (1996) Virology 220, 128–140). This phenomenon was not seen in the experiments; mice that received multiple injections of VLPs in either Freund's adjuvant or PBS alone developed similar CTL responses (FIG. 3). However, the present data suggests that the addition of adjuvant is unnecessary and can be avoided. It is hypothesized that the particulate nature of the VLPs may have caused the mice to develop CTL, but not antibody responses to SU epitopes. Other studies have shown that particulate antigens are powerful inducers of CTL responses (Layton, G. T., et al. (1996) Immunology 87, 171–178; Shirmbeck R. et al. (1996) Intervirology 39, 111–119; Wagner, R. et al. (1996) Virology 220, 128–140). The work of Schirmbeck and colleagues (Shirmbeck R., et al. (1996) Intervirology 39, 111–119) indicates that complex antigens such as VLPs are processed by an endocytic pathway in the context of MHC class I antigens. Dendritic cells and macrophages rapidly processed low doses of VLPs composed of hepatitis B virus small surface antigen for in vivo stimulation of syngeneic CD3$^+$ CD4$^-$CD8$^+$ CTL effector cells. In the case of the HIV VLPs examined in the present study, the packaging of the SU fusion protein within the particles may have rendered the SU epitopes inaccessible to the Class II-dependent stimulation of humoral immune responses and facilitated Class I-associated processing and presentation of the antigen. Taken together with recent studies which emphasize the potential importance of a strong antiviral CTL response and perhaps a weaker humoral response in the control of HIV infection (Rinaldo, C., et al. (1995) *J. Virol* 69, 5838–5842), the ability of the Gag-SU VLPs to generate this type of immune response in the absence of adjuvants suggests the importance of further investigation using primate or human systems. The success of packaging relatively large peptides using the frameshift approach suggests that a selection of nonviral proteins, including cancer-related antigens, may also be packaged into VLPs for presentation to the cellular arm of the immune system.

Many vaccines have been developed that are effective in controlling the pathogenesis and spread of a large number of viruses (reviewed by Hilleman, M. R., *AIDS Res. and Hu. Ret.,* 8: 1743–1747 (1992)). Rather than provide sterilizing immunity against the initial infection, vaccines typically stimulate immune responses that are re-activated during the initial phase of infection to expedite the control of viral infection. Retroviral integration into genomic DNA and the apparent infection of cells that are inaccessible to the majority of the immune system appear to complicate the development of a vaccine that would prevent AIDS (Hoth, D. F. et al. (1994) *Ann. Intern. Med.* 121, 603–611). However, investigations into disease-free individuals exposed to HIV by either repeated sexual contact or mother-to-infant routes suggest that vaccination may provide some immunity (Clerici, M. et al. (1993) *AIDS* 7, 1427–1433; and Clerici, M. et al. (1992) *J. Inf. Dis.* 165, 1012–1019). In addition, the inoculation of infected individuals with antigenic material may generate a therapeutic immune response (Salk, J., (1987) *Nature* (London) 327, 473–476; Burke, D. S. (1993) *Vaccine* 11 883–91; Birx, D. L. et al. (1993) *Curr. Opin. Immunol.* 5, 600–607). Analyses of long-term survivors and disease-free, exposed individuals implicate the benefits of strong CTL responses in the putative prevention or control of HIV infection (Paul, W. E. (1995) *Cell* 82, 177–82). The stimulation of Gag- and Env-specific murine CTL responses by the inoculation of chimeric Gag-SU VLPs suggests that these particle, or their derivatives, may provide such a therapeutic or preventative immune stimulation. Further elucidation of the immunological responses to HIV proteins in long-term survivors and disease-free, exposed individuals should continue to guide the development of effective vaccines and post-infection immunotherapies.

All publications and patent applications cited in this specification are herein incorporated by reference as if each individual publication or patent application were specifically and individually indicated to be incorporated by reference in its entirety for all purposes. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A recombinant chimeric nucleic acid, comprising:
   a retroviral gag sequence;
   a target nucleic acid sequence derived from a nucleic acid encoding a fusion partner selected from the group consisting of Env, an interleukin, TNF, GM/CSF, a nonretroviral viral antigen and a cancer antigen;
   wherein the gag and target sequences are transcribed from a single start site of transcription, and wherein the gag and target sequences are in different reading frames; and,
   a frame-shift site.

2. The recombinant chimeric nucleic acid of claim 1, wherein the target nucleic acid sequence is derived from a nucleic acid encoding a fusion partner selected from the group consisting of IL-1, IL-2, IL-4, IL-6, MART-1, gp 100, tyrosinase, bcl-1, bcl-2, c-myc, int-2, hst-1, ras, p53, prostate-specific membrane antigen, papilloma virus protein L1, protein kinase C., and G proteins.

3. The recombinant chimeric nucleic acid of claim 1, wherein the frame shift site is derived from a site selected from the group consisting of a retroviral frame shift site, a retrotransposon frame shift site, a human astrovirus frame shift site, a mouse intracisternal particle frame shift site, an HERV frame shift site, a Ty element frame shift site, and an optimized synthetic frameshift site.

4. A recombinant chimeric gag-env nucleic acid, comprising:
   a retroviral gag sequence;
   a retroviral env sequence;
   wherein the gag and env sequences are transcribed from a single start site of transcription, and wherein the gag and env sequences are in different reading frames; and,
   a retroviral frame-shift site derived from a retroviral gag-pol frame shift site.

5. The recombinant nucleic acid of claim 4, wherein the env sequence encodes approximately the carboxyl 65% of Env protein.

6. The recombinant nucleic acid of claim 4, wherein the nucleic acid further comprises a pol sequence.

7. The recombinant nucleic acid of claim 4, wherein the nucleic acid is a subsequence in a baculoviral vector.

8. The recombinant nucleic acid of claim 4, wherein the nucleic acid is competent to produce pseudovirions in an insect cell.

9. The recombinant nucleic acid of claim 4, wherein the nucleic acid is competent to produce pseudovirions in an insect cell, and wherein the nucleic acid hybridizes under stringent conditions to HIV Gag-fs-SU.

10. The recombinant nucleic acid of claim 4, wherein the nucleic acid is HIV Gag-fs-SU or a conservative variation thereof.

11. The recombinant nucleic acid of claim 4, wherein the nucleic acid is HIV Gag-fs-SU.

12. The recombinant nucleic acid of claim 4, wherein the nucleic acid is a subsequence in a baculoviral vector, wherein the vector is competent to transduce an insect cell.

13. The recombinant nucleic acid of claim 4, wherein the gag and env sequences are derived from HIV.

14. The recombinant nucleic acid of claim 4, wherein the nucleic acid further comprises a polyhedrin promoter.

15. The recombinant nucleic acid of claim 4, wherein the nucleic acid further comprises an SV 40 polyadenylation site.

16. A pseudovirion comprising a retroviral Gag protein and a fusion partner, wherein the fusion partner is present in a Gag-fs-fusion partner fusion protein.

17. The pseudovirion of claim 16, wherein the fusion partner is derived from a protein selected from the group consisting of an interleukin, TNF, GM/CSF, a nonretroviral viral antigen, a cancer antigen and a molecule involved in signal transduction.

18. The pseudovirion of claim 17, wherein the fusion partner is derived from a protein selected from the group consisting of IL-1, IL-2, IL-4, IL-6, MART-1, gp 100, tyrosinase, bcl-1, bcl-2, c-myc, int-2, hst-1, ras, p53, prostate-specific membrane antigen, papilloma virus protein L1, protein kinase C., and G proteins.

19. The pseudovirion of claim 16, wherein the fusion partner is derived from a retroviral Env protein.

20. The pseudovirion of claim 16, wherein the pseudovirion is noninfectious.

21. The pseudovirion of claim 19, wherein the Env protein domain is present primarily in the interior of the pseudovirion.

22. The pseudovirion of claim 19, wherein the Gag-fs-Env fusion protein is the Gag-fs-SU fusion protein, or a conservative modification thereof.

23. The pseudovirion of claim 19, wherein the Gag-fs-Env fusion protein is the Gag-fs-SU fusion protein.

24. The pseudovirion of claim 19, wherein the Env fusion partner is present in a Gag-fs-Env fusion protein, and wherein Gag protein is separately present in the fusion protein and as an independent protein.

25. The pseudovirion of claim 19, wherein the pseudovirion is made by transducing an insect cell with a baculovirus vector, which vector encodes a Gag-fs-Env protein.

26. The pseudovirion of claim 19, wherein the pseudovirion, when administered as an immunogenic composition in mice, elicits a CTL response against Env, but does not elicit antibodies which recognize Env.

27. An immunogenic composition comprising a pseudovirion comprising a retroviral Gag protein and a retroviral fusion partner, wherein the fusion partner is present in a Gag-fs-fusion partner fusion protein and wherein the fusion partner is derived from a retroviral Env protein.

28. The immunogenic composition of claim 27, wherein the immunogenic composition, when administered to mice, elicits a CTL response against Env, but does not elicit antibodies against Env.

29. A particulate vaccine comprising a pseudovirion comprising a retroviral Gag protein and a retroviral fusion partner, wherein the fusion partner is present in a Gag-fs-fusion partner fusion protein and wherein the fusion partner is derived from a retroviral Env protein.

30. The particulate vaccine of claim 29, wherein the vaccine, when administered to mice, elicits a CTL response against Env, but does not elicit antibodies against Env.

31. A fusion protein comprising a retroviral Gag sequence, a translation reading frame switching sequence and a fusion partner.

32. The fusion protein of claim 31, wherein the fusion partner is a retroviral Env amino acid subsequence.

33. The fusion protein of claim 31, wherein the fusogenic partner is selected from the group consisting of Env, an interleukin, TNF, GM/CSF, a nonretroviral viral antigen, a cancer antigen and a molecule involved in signal transduction.

34. The fusion protein of claim 31, wherein the fusogenic partner is selected from the group consisting of IL-1, IL-2, IL-4, IL-6, MART-1, gp 100, tyrosinase, bcl-1, bcl-2, c-myc, int-2, hst-1, ras, p53, prostate-specific membrane antigen, papilloma virus protein L1, protein kinase C. and G proteins.

35. The fusion protein of claim 32, wherein the Env amino acid subsequence comprises the carboxyl 65% of a retroviral Env protein.

36. The fusion protein of claim 32, wherein the Env amino acid subsequence is derived from HIV.

37. The fusion protein of claim 31, wherein the translation reading frame switching sequence comprises sequences derived from the N-terminus of a retroviral Pol protein.

38. A method of making a pseudovirion comprising expressing a nucleic acid encoding a Gag-fs-fusion partner fusion protein in a cell, wherein the cell translates the nucleic acid into a first protein comprising a Gag sequence, and a second protein comprising a gag sequence and a fusogenic partner.

39. The method of claim 38, wherein the fusogenic partner comprises an env sequence.

40. The method of claim 38, wherein the cell is an insect cell.

41. The method of claim 38, wherein the method further comprises the step of purifying the pseudovirion.

42. A pseudovirion comprising a retroviral Gag protein and a fusion partner, wherein the fusion partner is present in Gag-fs-fusion partner fusion protein and wherein the fusion partner is derived from retroviral Env protein.

43. A fusion protein comprising a retroviral Gag sequence, a translation reading frame switching sequence and a retroviral Env amino acid subsequence.

* * * * *